United States Patent [19]

Böshagen et al.

[11] Patent Number: 4,827,032

[45] Date of Patent: May 2, 1989

[54] CYCLOALKYL-ONE-CONTAINING BENZENESULPHONAMIDES

[75] Inventors: Horst Böshagen, Haan; Ulrich Rosentreter, Wuppertal; Folker Lieb, Leverkusen; Hermann Oediger, Cologne; Friedel Seuter; Elisabeth Perzborn, both of Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 212,840

[22] Filed: Jun. 29, 1988

Related U.S. Application Data

[63] Continuation of Ser. No. 13,302, Feb. 10, 1987, abandoned.

[30] Foreign Application Priority Data

Feb. 21, 1986 [DE] Fed. Rep. of Germany ....... 3605566
Sep. 19, 1986 [DE] Fed. Rep. of Germany ....... 3631824

[51] Int. Cl.⁴ .......................................... C07C 143/78
[52] U.S. Cl. ..................................... 564/90; 548/448; 548/449; 564/85; 564/86; 564/89
[58] Field of Search .......................................... 564/90

[56] References Cited

PUBLICATIONS

Kretov et al., *Chemical Abstracts*, vol. 59 (1963), 13865g.

*Primary Examiner*—Robert W. Ramsuer
*Attorney, Agent, or Firm*—Sprung Horn Kramer & Woods

[57] ABSTRACT

Cycloalkanol[1,2-b]indole-sulphonamides of the formula

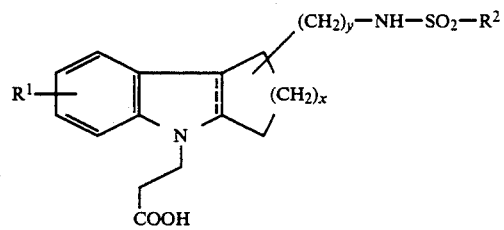

where appropriate in an isomeric form, and their salts are disclosed. These compounds are useful to inhibit platelet aggregation and to antagonize thromboxane $A_2$.

2 Claims, No Drawings

CYCLOALKYL-ONE-CONTAINING BENZENESULPHONAMIDES

This is a continuation of application Ser. No. 013,302, filed Feb. 10, 1987, now abandoned.

The invention relates to new cycloalkano[1,2-b]-indole-sulphonamides to process for their preparation and to their use in medicaments. (Benzenesulphonamidoalkyl)cycloalkano[1,2-b]indoles, which are likewise new, can be used as intermediates for the preparation of the new compounds.

New cycloalkano[1,2-b]indole-sulphonamides of the general formula (I)

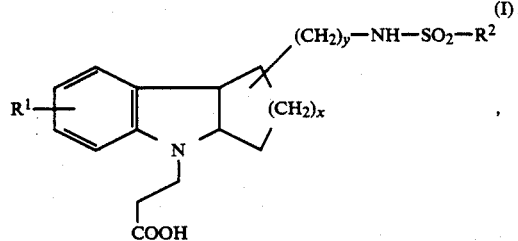

in which

R$^1$ represents hydrogen, halogen, trifluoromethyl, carboxyl or alkoxycarbonyl; or represents a group of the formula —S(O)$_m$R$^3$,
in which
R$^3$ denotes alkyl or aryl, and
m denotes one of the numbers 0, 1 or 2; or represents a group of the formula

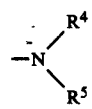

in which
R$^4$ and R$^5$ are identical or different and represent hydrogen, alkyl, aryl, aralkyl or acetyl; or represents a group of the formula —OR$^6$,
in which
R$^6$ denotes hydrogen, alkyl, aryl, aralkyl, alkyl-SO$_2$—, aryl-SO$_2$—, aralkyl-SO$_2$— or trifluoromethyl; or represents alkyl, alkenyl or cycloalkyl, each of which is optionally substituted by carboxyl, alkoxycarbonyl, halogen, hydroxyl, alkoxy, alkylthio or cyano,
R$^2$ represents aryl which is optionally substituted up to 5 times by halogen, cyano, trifluoromethyl, trifluoromethoxy, trifluoromethylthio, alkyl, carboxyalkyl, alkoxycarbonylalkyl, alkoxy, alkylthio, hydroxyl, carboxyl, alkoxycarbonyl, phenyl, phenoxy, benzyloxy, benzylthio or by a group of the formula

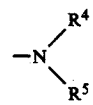

in which
R$^4$ and R$^5$ have the abovementioned meaning,
x represents the number 1, 2 or 3, and
y represents the number 0 or 1, where appropriate in an isomeric form, and their salts, have been found.

The cycloalkano[1,2-b]indole-sulphonamides according to the invention have several asymmetric carbon atoms and can thus exist in various stereochemical forms. The invention relates both to the individual isomers and to the mixtures thereof.

The following isomeric forms of the cycloalkano-[1,2-b]indole-sulphonamides may be mentioned by way of example:

(a) Cycloalkano[1,2-b]indole-sulphonamides

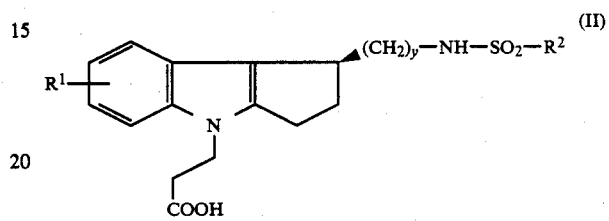

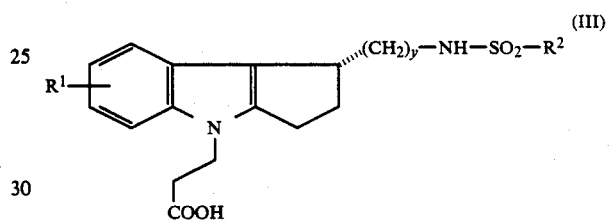

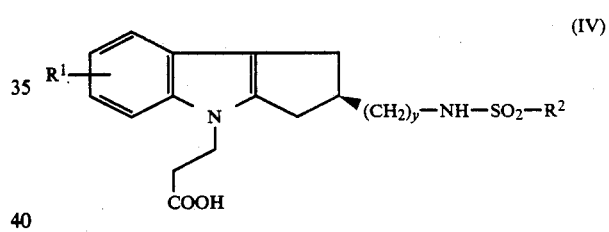

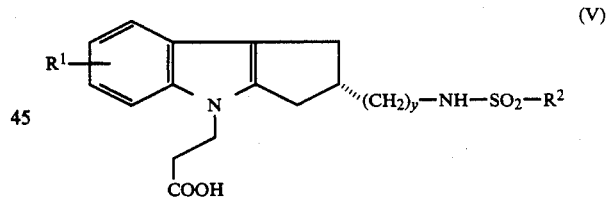

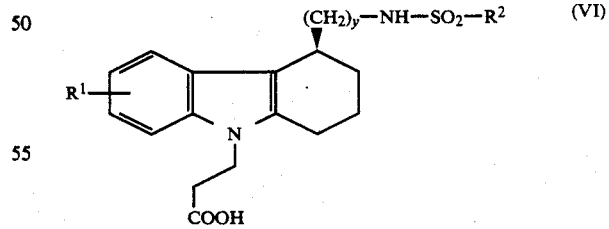

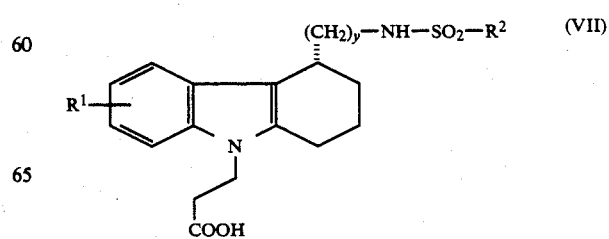

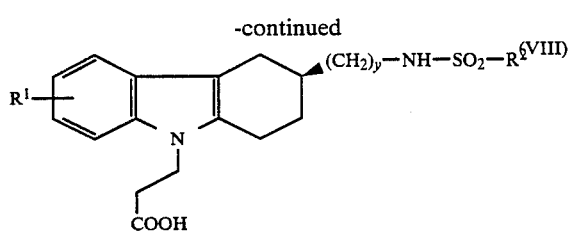

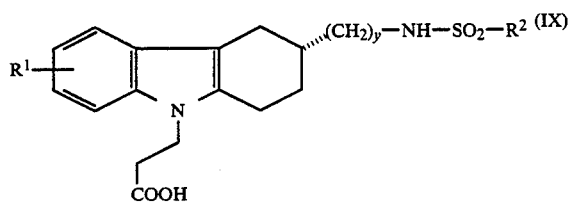

(b) Cycloalkano[1,2-b]dihydroindole-sulphonamides

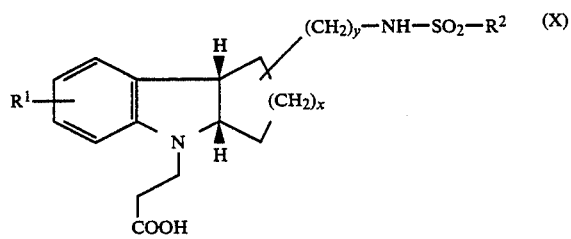

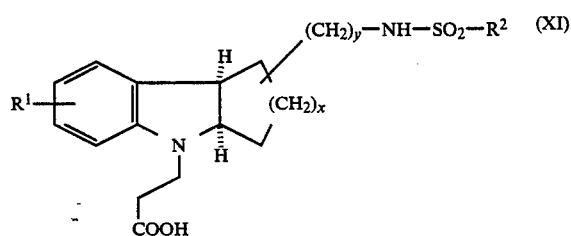

$R^1$, $R^2$, x and y having the abovementioned meaning.

The cycloalkano[1,2-b]indole-sulphonamides according to the invention can also be in the form of their salts. In general, the salts which may be mentioned in this context are those with organic or inorganic bases.

Physiologically acceptable salts are preferred within the scope of the present invention. Physiologically acceptable salts of the cycloalkano[1,2-b]indole-sulphonamides can be metal or ammonium salts of the substances according to the invention which have a free carboxyl group. Examples of those which are particularly preferred are sodium, potassium, magnesium or calcium salts, as well as ammonium salts which are derived from ammonia or organic amines such as, for example, ethylamine, di- or triethylamine, di- or triethanolamine, dicyclohexylamine, dimethylaminoethanol, arginine or ethylenediamine.

The substances according to the invention surprisingly exhibit an action inhibiting platelet aggregation and can be used for the therapeutic treatment of humans Alkyl generally represents a straight-chain or branched hydrocarbon radical having 1 to 12 carbon atoms. Lower alkyl having 1 to 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl generally represents a straight-chain or branched hydrocarbon radical having 2 to 12 carbon atoms and one or more, preferably having one or two, double bonds. The lower alkenyl radical having 2 to 6 carbon atoms and one double bond is preferred. An alkenyl radical having 2 to 4 carbon atoms and one double bond is particularly preferred. Examples which may be mentioned are vinyl, allyl, propenyl, isopropenyl, butenyl, isobutenyl, pentenyl, isopentenyl, hexenyl, isohexenyl, heptenyl, isoheptenyl, octenyl and isooctenyl.

Cycloalkyl generally represents a cyclic hydrocarbon radical having 3 to 8 carbon atoms. The cyclopentane and the cyclohexane ring is preferred. Examples which may be mentioned are cyclopropyl, cyclopentyl, cyclohexyl, cycloheptyl and cyclooctyl.

Alkoxy generally represents a straight-chain or branched hydrocarbon radical which has 1 to 12 carbon atoms and is bonded via an oxygen atom. Lower alkoxy having 1 to 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio generally represents a straight-chain or branches hydrocarbon radical which has 1 to 12 carbon atoms and is bonded via a sulphur atom. Lower alkylthio having 1 to 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Aryl generally represents an aromatic radical having 6 to 12 carbon atoms. Preferred aryl radicals are phenyl, naphthyl and diphenyl.

Aralkyl generally represents an aryl radical which has 7 to 14 carbon atoms and is bonded via an alkylene chain. Aralkyl radicals having 1 to 6 carbon atoms in the aliphatic part and 6 to 12 carbon atoms in the aromatic part are preferred. Examples which may be mentioned are the following aralkyl radicals: benzyl, naphthylmethyl, phenethyl and phenylpropyl.

Alkoxycarbonyl can be represented by, for example, the formula

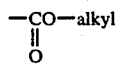

In this, alkyl represents a straight-chain or branched hydrocarbon radical having 1 to 8 carbon atoms. Lower alkoxycarbonyl having 1 to 6 carbon atoms in the alkyl part is preferred. An alkoxycarbonyl having 1 to 4 carbon atoms in the alkyl part is particularly preferred. Examples which may be mentioned are the following alkoxycarbonyl radicals: methoxycarbonyl, ethoxycarbonyl, propoxycarbonyl, isopropoxycarbonyl, butoxycarbonyl and isobutoxycarbonyl.

Carboxyalkyl generally represents a straight-chain or branched hydrocarbon radical which has 1 to 12 carbon atoms and is substituted by a carboxyl group. Carboxylower-alkyl having 1 to 6 carbon atoms is preferred. Examples which may be mentioned are: carboxymethyl, 1-carboxyethyl, 1-carboxypropyl, 1-carboxybutyl, 1-carboxypentyl, 1-carboxyhexyl, 2-carboxyethyl, 2-carboxypropyl, 2-carboxybutyl, 3-carboxypropyl, 3-carboxybutyl, 4-carboxybutyl, 2-carboxy-1-propyl and 1-carboxy-1-propyl.

Alkoxycarbonylalkyl generally represents a straight-chain or branched hydrocarbon radical which has 1 to 12 carbon atoms and is substituted by an alkoxycarbonyl group, alkoxycarbonyl having the abovementioned meaning. Lower alkoxycarbonyl-lower-alkyl having 1 to 6 carbon atoms in each alkyl part is preferred. Examples which may be mentioned are: methoxycarbonylmethyl, ethoxycarbonylmethyl, propoxycarbonylmethyl, butoxycarbonylmethyl, isopropoxycarbonylmethyl, isobutoxycarbonylmethyl, 1-methoxycarbonylethyl, 1-ethoxycarbonylethyl, 1-propoxycarbonylethyl, 1-butoxycarbonylethyl, 1-isopropoxycarbonylethyl, 1-isobutoxycarbonylethyl, 2-methoxycarbonylethyl, 2-ethoxycarbonylethyl, 2-propoxycarbonylethyl, 2-butoxycarbonylethyl, 2-isopropoxycarbonylethyl, 2-isobutoxycarbonylethyl, 2-methoxycarbonyl-2-propyl, 2-ethoxycarbonyl-2-propyl, 2-propoxycarbonyl-2-propyl, 2-butoxycarbonyl-2-propyl, 2-isopropoxycarbonyl-2-propyl, 2-isobutoxycarbonyl-2-propyl, 2-methoxycarbonyl-2-propyl, 1-ethoxycarbonyl-2-propyl, 2-propoxycarbonyl-2-propyl, 1-butoxycarbonyl-2-propyl, 1-isopropoxycarbonyl-2-propyl, 1-isobutoxycarbonyl-2-propyl, 3-methoxycarbonylpropyl, 3-ethoxycarbonylpropyl, 3-isopropoxycarbonylpropyl and 3-isobutoxycarbonylpropyl.

Halogen generally represents fluorine, chlorine, bromine or iodine, preferably fluorine, chlorine or bromine. Halogen particularly preferably represents fluorine or chlorine.

The compounds of the general formula (I) which are preferred are those in which $R^1$ represents hydrogen, fluorine, chlorine, bromine, trifluoromethyl, carboxyl or lower alkoxycarbonyl; or represents a group of the formula

—S(O)$_m$R$^3$ in which $R^3$ denotes lower alkyl or phenyl, and m denotes a number 0 or 2; or represents a group of the formula

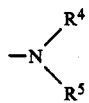

in which $R^4$ and $R^5$ are identical or different and denote hydrogen, lower alkyl, phenyl, benzyl or acetyl; or represents a group of the formula —OR$^6$, in which $R^6$ denotes hydrogen, lower alkyl, phenyl, phenyl-SO$_2$—, methyl-SO$_2$—, ethyl-SO$_2$— or trifluoromethyl; or represents lower alkyl, lower alkenyl, cyclopentyl, or cyclohexyl, each of which is optionally substituted by carboxyl, methoxycarbonyl, ethoxycarbonyl, fluorine, chlorine, bromine, hydroxyl, lower alkoxy or cyano.

$R^2$ represents phenyl which is optionally substituted up to three times by fluorine, chlorine, bromine, cyano, trifluoromethyl, trifluoromethoxy, trifluoromethylthio, lower alkyl, carboxymethyl, carboxyethyl, methoxymethyl, ethoxymethyl, methoxyethyl, ethoxyethyl, lower alkoxy, lower alkylthio, hydroxyl, carboxyl, lower alkoxycarbonyl, phenyl, phenoxy, benzyloxy, benzylthio or by the group

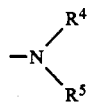

in which $R^4$ and $R^5$ have the meaning already indicated, x represents the number 1, 2 or 3, and y represents the number 0 or 1, where appropriate in an isomeric form, and their salts.

The compounds of the general formula (I) which are particularly preferred are those in which $R^1$ represents hydrogen, fluorine, chlorine, bromine, trifluoromethyl, methylthio, ethylthio, methylsulphonyl, phenylthio, phenylsulphonyl, amino, dimethylamino, diethylamino or acetylamino; or represents a group of the formula

—OR$^6$, in which $R^6$ denotes hydrogen, C$_1$—C$_4$-alkyl, phenyl or benzyl; or represents C$_1$—C$_4$-alkyl, $R^2$ represents phenyl which is substituted up to three times, identically or differently, by fluorine, chlorine, bromine, cyano, trifluoromethyl, trifluoromethoxy, C$_1$—C$_4$-alkyl, C$_1$—C$_4$-alkoxy, methylthio, hydroxyl, methoxycarbonyl, ethoxycarbonyl, dimethylamino, acetylamino, or diethylamino, x represents the number 1 or 2, and y represents the number 0 or 1, where appropriate in an isomeric form, and their salts.

The compounds of the general formula (I) which are very particularly preferred are those in which $R^1$ represents hydrogen, fluorine, methyl, methoxy, benzyloxy or hydroxyl, $R^2$ represents phenyl which is substituted by fluorine, chlorine, trifluoromethyl, methyl, ethyl, propyl, isopropyl or methoxy, x represents the number 1 or 2, and y represents the number 0 or 1, where appropriate in an isomeric form, and their salts.

Particularly preferred are (+)- or (—)-isomeric cycloalkano[1,2-b]indole-sulphonamides of the formula

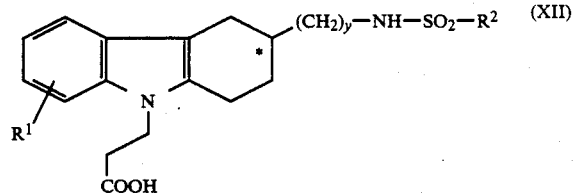

in which $R^1$ represents hydrogen, fluorine, methyl, methoxy, benzyloxy or hydroxyl, $R^2$ represents phenyl which is substituted by fluorine, chlorine, trifluoromethyl, methyl, propyl, isopropyl or methoxy, and y represents the number 0 or 1, and their salts.

The following cycloalkano[1,2-b]indole-sulphonamides may be mentioned by way of example:

1-(benzenesulphonamidomethyl)-4-(2-carboxyethyl)cyclopentano[1,2-b]indole 4-(2-carboxyethyl)-1-(4-fluorophenylsulphonamidomethyl)cyclopentano[1,2-b]indole 4-(2-carboxyethyl)-1-(4-chlorophenylsulphonamidomethyl)cyclopentano[1,2-b]indole
1-(benzenesulphonamidomethyl)-4-(2-carboxyethyl)-7-methoxycyclopentano[1,2-b]indole
4-(2-carboxyethyl)-1-(4-fluorophenylsulphonamidomethyl)-7-methoxycyclopentano[1,2-b]indole
4-(2-carboxyethyl)-1-(4-chlorophenylsulphonamidomethyl)-7-methoxycyclopentano[1,2-b]indole
1-(benzenesulphonamido)-4-(2-carboxyethyl)cyclopentano-[1,2-b]indole
4-(2-carboxyethyl)-1-(4-fluorophenylsulphonamido)cyclopentano[1,2-b]indole
4-(2-carboxyethyl)-1-(4-chlorophenylsulphonamido)cyclopentanto[1,2-b]indole
1-(benzenesulphonamido)-4-(2-carboxyethyl)-7-methoxycyclopentano[1,2-b]indole
4-(2-carboxyethyl)-1-(4-fluorophenylsulphonamido)-7-methoxycyclopentano[1,2-b]indole
4-(2-carboxyethyl)-1-(4-chlorophenylsulphonamido)-7-methoxycyclopentano[1,2-b]indole
1-(benzenesulphonamidomethyl)-4-(2-carboxyethyl)-7-methylcyclopentano[1,2-b]indole
4-(2-carboxyethyl)-1-(4-fluorophenylsulphonamidomethyl)-7-methylcyclopentano[1,2-b]indole
4-(2-carboxyethyl)-1-(4-chlorophenylsulphonamidomethyl)-7-methylcyclopentano[1,2-b]indole
1-(benzenesulphonamido)-4-(2-carboxyethyl)-7-methylcyclopentano[1,2-b]indole
4-(2-carboxyethyl)-1-(4-fluorophenylsulphonamido)-7-methylcyclopentano[1,2-b]indole
4-(2-carboxyethyl)-1-(4-chlorophenylsulphonamido)-7-methylcyclopentano[1,2-b]indole
4-(2-carboxyethyl)-1-(4-tolylsulphonamidomethyl)-cyclopentano[1,2-b]indole
4-(2-carboxyethyl)-1-(4-tolylsulphonamido)-cyclopentano-[1,2-b]indole
3-r-(benzenesulphonamido)-9-(2-carboxyethyl)-6-methoxy-1,2,3,4,4a–t,9a–t-hexahydrocarbazole
3-r-(benzenesulphonamido)-9-(3-carboxyethyl)-6-methoxy-1,2,3,4,4a–c,9a–c-hexahydrocarbazole
3-r-(benzenesulphonamidomethyl)-9-(2-carboxyethyl)-1,2,3,4,4a–t,9a–t-hexahydrocarbazole
3-r-(benzenesulphonamidomethyl)-9-(2-carboxyethyl)-1,2,3,4,4a–c,9a–c-hexahydrocarbazole
3-r-(benzenesulphonamidomethyl)-9-(2-carboxyethyl)-6-methoxy-1,2,3,4,4a–t,9a–t-hexahydrocarbazole
3-r-(benzenesulphonamidomethyl)-9-(2-carboxyethyl)-6-methoxy-1,2,3,4,4a–c,9a–c-hexahydrocarbazole
9-(2-carboxyethyl)-3-r-(4-chlorophenylsulphonamido)-1,2,3,4,4a–t,9a–t-hexahydrocarbazole
9-(2-carboxyethyl)-3-r-(4-chlorophenylsulphonamido)-1,2,3,4,4a–c,9a–c-hexahydrocarbazole
9-(2-carboxyethyl)-3-r-(4-fluorophenylsulphonamido)-1,2,3,4,4a–t,9a–t-hexahydrocarbazole
9-(2-carboxyethyl)-3-r-(4-fluorophenylsulphonamido)-1,2,3,4,4a–c,9a–c-hexahydrocarbazole,
9-(2-carboxyethyl)-3-r-(4-tolylsulphonamido)-1,2,3,4,4a–t,9a–t-hexahydrocarbazole
9-(2-carboxyethyl)-3-r-(4-tolylsulphonamido)-1,2,3,4,4a–c,9a–c-hexahydrocarbazole
9-(2-carboxyethyl)-3-r-(4-fluorophenylsulphonamido)-6-methoxy-1,2,3,4,4a–t,9a–t-hexahydrocarbazole
9-(2-carboxyethyl)-3-r-(4-fluorophenylsulphonamido)-6-methoxy-1,2,3,4,4a–c-9a–c-hexahydrocarbazole
(+)-3-(4-chlorophenylsulphonamido)-9-(2-carboxyethyl)-1,2,3,4-tetrahydrocarbazole
(+)-3-(4-fluorophenylsulphonamido)-9-(2-carboxyethyl)-1,2,3,4-tetrahydrocarbazole
(−)-3-(4-chlorophenylsulphonamido)-9-(2-carboxyethyl)-1,2,3,4-tetrahydrocarbazole
(−)-3-(4-fluorophenylsulphonamido)-9-(2-carboxyethyl)-1,2,3,4-tetrahydrocarbazole
(±)-3-(4-chlorophenylsulphonamido)-9-(2-carboxyethyl)-1,2,3,4-tetrahydrocarbazole
(±)-3-(4-fluorophenylsulphonamido)-9-(2-carboxyethyl)-1,2,3,4-tetrahydrocarbazole.

Particularly preferred are: (+)-3-(4-fluorophenyl-sulphonamido)-9-(2-carboxyethyl)-1,2,3,4-tetrahydrocarbazole and (−)-3-(4-fluorophenyl-sulphonamido)-9-(2-carbonylethyl)-1,2,3,4-tetrahydrocarbazole.

Furthermore, a process for the preparation of the cycloalkano[1,2-b]indole-sulphonamides according to the invention, and of their salts, has been found, which is characterized in that (benzenesulphonamidoalkyl)cycloalkano[1,2-b]indoles of the general formula (XIII)

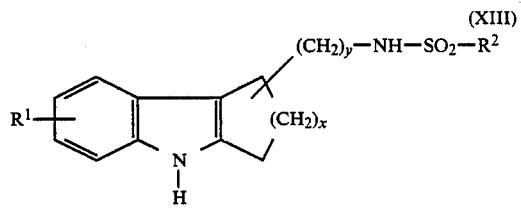

in which

R$^1$ represents hydrogen, halogen, trifluoromethyl, carboxyl or alkoxycarbonyl; or represents a group of the formula —S(O)$_m$R$^3$, in which R$^3$ denotes alkyl or aryl, and m denotes one of the numbers 0, 1 or 2; or represents a group of the formula

in which

R$^4$ and R$^5$ are identical or different and represent hydrogen, alkyl, aryl, aralkyl or acetyl; or represents a group of the formula —OR$^6$, in which R$^6$ denotes hydrogen, alkyl, aryl, aralkyl, alkyl-SO$_2$—, aryl-SO$_2$—, aralkyl-SO$_2$— or trifluoromethyl; or represents alkyl, alkenyl or cycloalkyl, each of which is optionally substituted by carboxyl, alkoxycarbonyl, halogen, hydroxyl, alkoxy, alkylthio or cyano, R$^2$ represents aryl which is optionally substituted up to 5 times by halogen, cyano, trifluoromethyl, trifluoromethoxy, trifluoromethylthio, alkyl, carboxylalkyl, alkoxycarbonylalkyl, alkoxy, alkylthio, hydroxyl, carboxyl, alkoxycarbonyl, phenyl, phenoxy, benzyloxy, benzylthio or by a group of the formula

in which

R$^4$ and R$^5$ have the abovementioned meaning, x represents the number 1, 2 or 3, and y represents the number 0 or 1, are reacted with acrylonitrile in the presence of an inert solvent, where appropriate in the presence of a base, then the N,N'-bis-cyanoethyl compounds are hydrolyzed, then, in the case where the cycloalkano[1,2-b]dihydroindole-sulphonamides are being prepared the cycloalkano[1,2-b]indole-sulphonamides are hydrogenated, where appropriate in the presence of an inert solvent, in the presence of an acid and of a reducing agent, where appropriate the isomers are separated in a customary manner, and then, where appropriate, in the case where the salts are being prepared reaction with an appropriate base is carried out.

The process according to the invention can be illustrated by the diagram which follows:

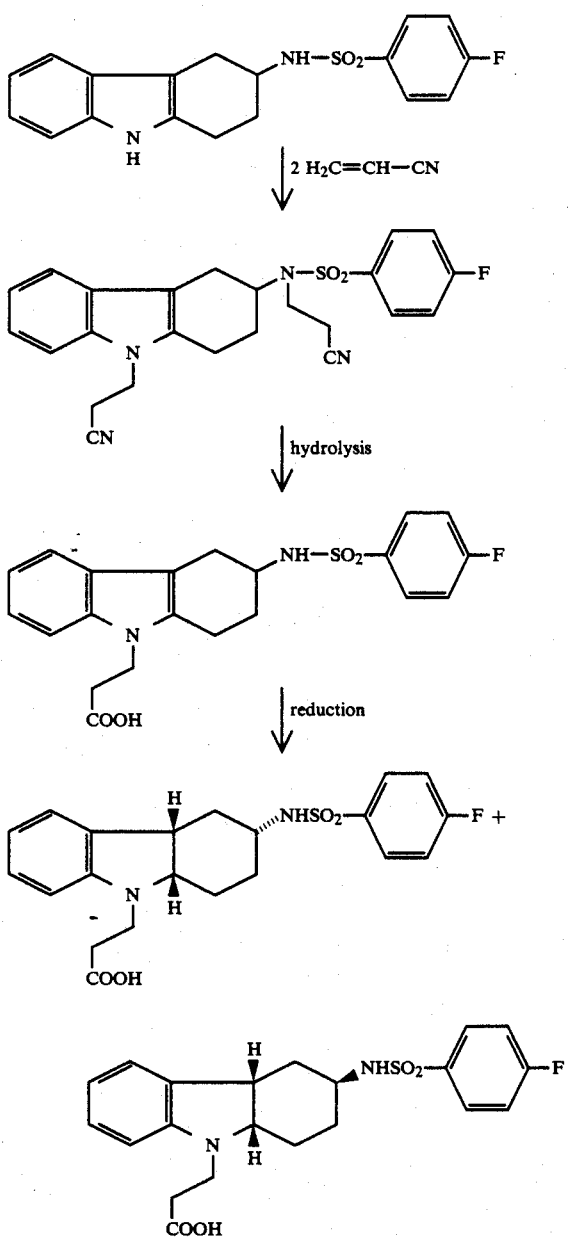

The cycloalkano[1,2-b]dihydroindole-sulphonamides within the scope of formula (I) correspond to the formula (Ia)

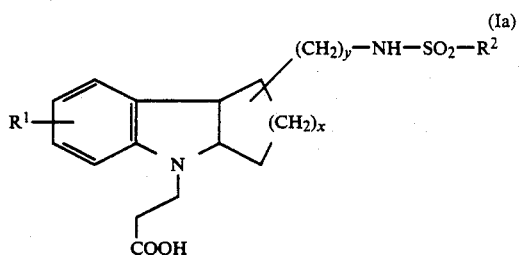

in which $R^1$, $R^2$, x and y have the abovementioned meaning.

When the process according to the invention is carried out, in general the intermediates produced can be isolated. Thus, it is possible to carry out the process according to the invention in several process stages. However, it may also be possible to combine various process steps.

Possible solvents for the process according to the invention are water and organic solvents which do not change under the reaction conditions. These preferably include alcohols such as methanol, ethanol, propanol or isopropanol, ethers such as diethyl ether, tetrahydrofuran, dioxane, glycol monomethyl or dimethyl ether, hydrocarbons such as benzene, toluene, xylene, cyclohexane, hexane or petroleum fractions, dimethyl sulphoxide, dimethylformamide, hexamethylphosphoric triamide, ethyl acetate, acetonitrile or pyridine. It is equally possible to use mixtures of the said solvents.

Possible bases for the process according to the invention are customary basic compounds. These preferably include alkali metal and alkaline earth metal hydroxides, such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alcoholates such as, for example, sodium methanolate or ethanolate, potassium methanolate or ethanolate, or potassium tert.-butylate, or amides such as sodamide or lithium diisopropylamide, or organic amines such as benzyltrimethylammonium hydroxide, tetrabutylammonium hydroxide, pyridine, triethylamine or N-methylpiperidine.

The process according to the invention is generally carried out in a temperature range from 0° C. to 150° C., preferably from 20° C. to 100° C.

The process according to the invention is generally carried out under atmospheric pressure. However, it is also possible to carry out the process under reduced pressure or elevated pressure (for example in a range from 0.5 to 5 bar).

In general, 1 to 20 mol, preferably 1 to 10 mol, of acrylonitrile is used for each mol of (benzenesulphonamidoalkyl)cycloalkano[1,2-b]indole.

The N,N'-bis-cyanoethyl compounds are hydrolyzed in a manner known per se in the presence of bases such as alkali metal or alkaline earth metal hydroxides or alkanolates, in inert solvents such as water or alcohols. The preferred bases which are used are sodium, potassium or barium hydroxide, sodium methanolate, potassium methanolate, sodium ethanolate or potassium ethanolate, preferably in water or methanol, ethanol, propanol or isopropanol, or in mixtures of these solvents.

In general 1 to 100 mol, preferably 2 to 50 mol, of base is used for each mol of N,N'-biscyanoethyl compound.

The hydrolysis is carried out in a temperature range from 0° C. to 100° C., preferably from 20° C. to 80° C.

The hydrogenation is carried out in a manner known per se. It is possible for the acid which is used to be employed as solvent for this.

Suitable solvents for the hydrogenation are inert organic solvents which do not change under the reaction conditions. These preferably include ethers such as diethyl ether, dioxane or tetrahydrofuran, or glacial acetic acid, trifluoroacetic acid, methanesulphonic acid or trifluoromethanesulphonic acid.

Acids which can be used for all the process steps according to the invention are organic acids. These preferably include carboxylic acids such as, for example, acetic acid, propionic acid, chloroacetic acid, dichloroacetic acid or trifluoroacetic acid, or sulfonic acids such as, for example, methanesulphonic acid, ethanesulphonic acid, toluenesulphonic acid or benzenesulphonic acid or trifluoromethanesulphonic acid.

Suitable reducing agents for the hydrogenation according to the invention are the customary reducing agents. These preferably include hydrides such as, for example, sodium borohydride, sodium cyanoborohydride, tetrabutylammonium borohydride, tetrabutylammonium cyanoborohydride, tributyltin hydride, triethylsilane, dimethylphenylsilane or triphenylsilane.

The hydrogenation is generally carried out in a temperature range from −40° C. to +80° C., preferably from −20° C. to +60° C.

The (benzenesulphonamidoalkyl)cycloalkano[1,2-b]-indoles of the general formula XIII which are used are new. A process for the preparation of the (benzenesulphonamidoalkyl)cycloalkano[1,2-b]indoles has likewise been found, which is characterized in that phenylhydrazines of the general formula (XIV)

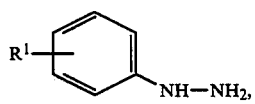

(XIV)

in which

R¹ has the abovementioned meaning, are reacted with cycloalkanonesulphonamides of the general formula (XV)

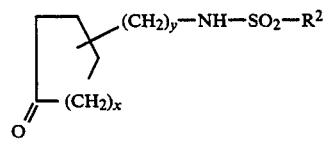

(XV)

in which

R², x and y have the abovementioned meaning, in the presence of inert solvents and, where appropriate, in the presence of a catalyst.

The preparation of the (benzenesulphonamidoalkyl)-cycloalkano[1,2-b]indoles according to the invention can be illustrated by the diagram which follows:

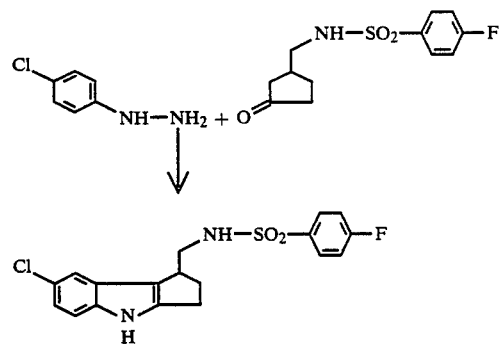

Possible solvents for the process according to the invention here are inert organic solvents which do not change under the reaction conditions. These preferably include alcohols such as, for example, methanol, ethanol, n-propanol, iso-propanol and glycol, ethers such as, for example, diethyl ether, dioxane, tetrahydrofuran, glycol monomethyl or dimethyl ether, halogenated hydrocarbons such as di-, tri- or tetrachloromethane, dichloroethylene and trichloroethylene, ethyl acetate, toluene, acetonitrile, glacial acetic acid, hexamethylphosphoric triamide, pyridine and acetone. Of course, it is possible to use mixtures of the solvents.

Suitable catalysts for the process according to the invention are the customary acids or Lewis acids. These preferably include inorganic acids such as hydrochloric acid, hydrobromic acid or sulphuric acid, or organic acids such as carboxylic acids or sulphonic acids, for example acetic acid, methanesulphonic acid and toluenesulphonic acid, or Lewis acids such as, for example, zinc chloride, zinc bromide or boron trifluoride etherate.

The process according to the invention is generally carried out in a temperature range from 0° C. to 200° C., preferably from 20° C. to 150° C.

The process according to the invention is generally carried out under atmospheric pressure. It is equally possible to carry it out under elevated or reduced pressure (for example from 0.5 to 5 bar).

In general, the hydrazine is used in an amount of 1 to 3 mol, preferably 1 to 1.5 mol, relative to the ketone.

Examples of hydrazines which are used for the process according to the invention are: phenylhydrazine, 4-methoxyphenylhydrazine, 4-chlorophenylhydrazine, 4-fluorophenylhydrazine and 4-methylphenylhydrazine.

Examples of ketones which are used according to the invention are:
3-(benzenesulphonamidomethyl)cyclopentanone
3-(benzenesulphonamidomethyl)cyclohexanone
4-(benzenesulphonamidomethyl)cyclohexanone
3-(benzenesulphonamido)cyclopentanone
3-(benzenesulphonamido)cyclohexanone
4-(benzenesulphonamido)cyclohexanone
3-(4-chlorophenylsulphonamidomethyl)cyclopentanone
3-(4-fluorophenylsulphonamidomethyl)cyclopentanone
3-(4-methylphenylsulphonamidomethyl)cyclopentanone
3-(4-chlorophenylsulphonamidomethyl)cyclohexanone
3-(4-fluorophenylsulphonamidomethyl)cyclohexanone
3-(4-methylphenylsulphonamidomethyl)cyclohexanone
4-(4-chlorophenylsulphonamidomethyl)cyclohexanone 4-(4-fluorophenylsulphonamidomethyl)cyclohexanone
4-(methylphenylsulphonamidomethyl)cyclohexanone
3-(4-chlorophenylsulphonamido)cyclopentanone
3-(4-(fluorophenylsulphonamido)cyclopentanone
3-(4-methylphenylsulphonamido)cyclopentanone
3-(4-chlorophenylsulphonamido)cyclohexanone
3-(4-fluorophenylsulphonamido)cyclohexanone
3-(4-methylphenylsulphonamido)cyclohexanone
4-(4-chlorophenylsulphonamido)cyclohexanone
4-(4-fluorophenylsulphonamido)cyclohexanone
4-(4-methylphenylsulphonamido)cyclohexanone The hydrazines XIV which are used as starting materials are known or can be prepared by known methods (compare Houben-Weyl, "Methoden der organischen Chemie" (Methods of Organic Chemistry), X/2, page 1, 123, (693).

Some of the cyclohexanonesulphonamides of the general formula (XVa)

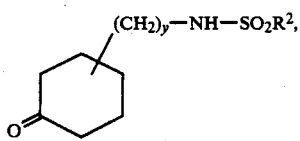

in which y and $R^2$ have the abovementioned meaning, which are used as starting materials are known, and they can be prepared by methods known per se (compare Houben-Weyl "Methoden der organischen Chemie", IX, 605; A. Mooradian et al., J. Med. Chem. 20 (4), 487 (1977)).

The cyclopentanonesulphonamides of the general formula (XVb)

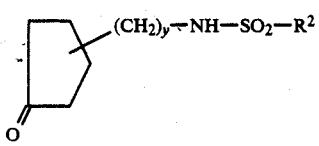

in which y and $R^2$ have the abovementioned meaning, which are used as starting materials are novel.

A process for the preparation of the new cycloalkanonesulphonamides has also been found, which is characterized in that cycloalkanols of the general formula (XVI)

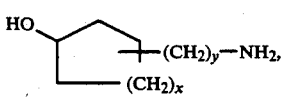

in which x and y have the abovementioned meaning, are reacted with sulphonyl halides of the general formula (XVII)

in which $R^{12}$ has the abovementioned meaning and

Hal represents fluorine, chlorine, bromine or iodine, preferably chlorine or bromine, in inert organic solvents and, where appropriate, in the presence of bases, and then oxidation in inert solvents is carried out.

The cycloalkanols can be prepared by reacting cycloalkenones (XVIII)

with nitromethane in inert organic solvents, where appropriate in the presence of bases, and then reducing the compounds (XIX)

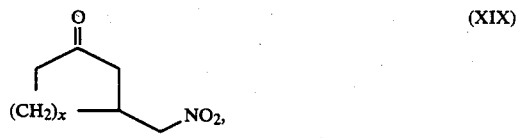

(CAa 92, 89, 849 and CA 87, 22 191).

The sulphonyl halides can be prepared by methods known per se (Houben-Weyl's "Methoden der organischen Chemie" IX, 564).

The preparation of the cycloalkano[1,2-b]indolesulphonamides according to the invention can be illustrated by the following reaction diagram:

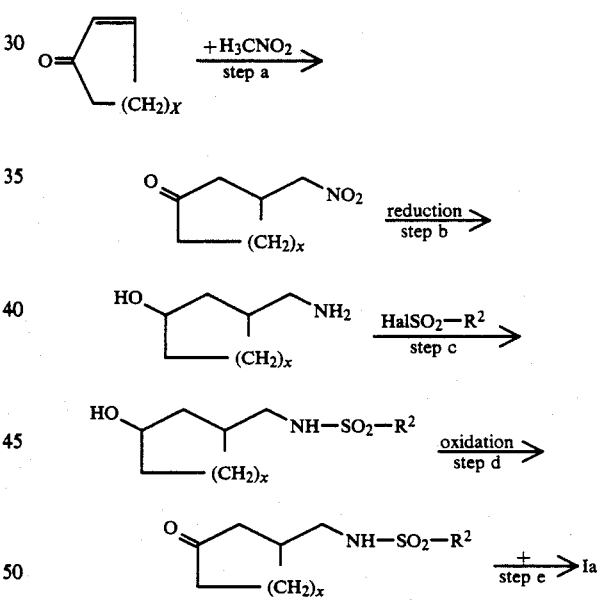

According to this, in the first step (a) cycloalkenones are reacted with nitro compounds such as nitromethane, in inert solvents such as alcohols, for example methanol, ethanol or propanol, or ethers, for example diethyl ether, tetrahydrofuran or dioxane, or chlorinated hydrocarbons, for example methylene chloride, chloroform or carbon tetrachloride, in the presence of bases such as, for example, sodium hydride, sodium or potassium methanolate, sodium or potassium ethanolate, potassium tert.-butanolate, 1,5-diazabicyclo[4.3.0]non-5-ene, 1,5-diazabicyclo[5.4.0]undec-5-ene, pyridine or triethylamine, at temperatures in the range from 0° C. to 100° C., to give nitro compounds.

In step (b) the nitro compounds are reduced in inert solvents such as ethers, for example tetrahydrofurn, dioxane or diethyl ether, in the presence of a reducing agent such as hydrides, for example LiAlH$_4$, Na[Al-(OCH$_2$CH$_2$—OCH$_3$)$_2$H$_2$] or di-iso-butyl-aluminumhydride, at temperatures in the range from $-20°$ C. to $+60°$ C. to give cycloalkanols.

In step (c) the cycloalkanols are converted with sulphonyl halides in inert solvents such as ethers, for example dioxane, tetrahydrofuran or diethyl ether, or chlorinated hydrocarbons such as methylene chloride, chloroform or carbon tetrachloride, or ethyl acetate or pyridine, where appropriate in the presence of bases such as 1,5-diazabicyclo[4.3.0]non-5-ene, 1,5-diazabicyclo[5.4.0]undec-5-ene, pyridine or triethylamine, at temperatures from $-20°$ C. to $+60°$ C., into sulphonamides.

In step (d), the sulphonamides are oxidized in inert solvents such as water, glacial acetic acid, acetone, pyridine or mixtures thereof, with oxidizing agents such as chromium(VI) compounds, for example CrO$_3$, K$_2$Cr$_2$O$_7$ or Na$_2$Cr$_2$O$_7$, at temperatures from $-20°$ C. to $+100°$ C., to give cycloalkanonesulphonamides.

In step (e) cycloalkanonesulphonamides (XVb) and hydrazines XIV are reacted as described above to give the corresponding (benzenesulphonamidoalkyl)cycloalkano[1,2-b]-indoles of the formula XIII

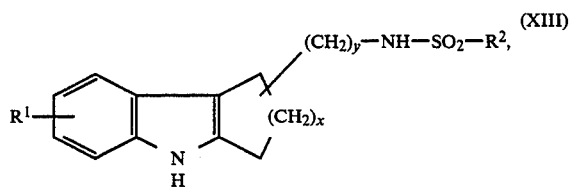

(XIII)

R$^1$, R$^2$, x and y have the abovementioned meaning.

The enantiomerically pure (benzenesulphonamido)cyclohexano[1,2-b]indoles of the general formula (XIIIa)

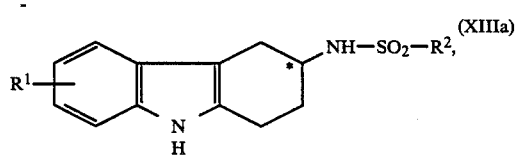

(XIIIa)

in which

R$^1$ and R$^2$ have the indicated meaning, are likewise new.

A process for the preparation of the enantiomerically pure (benzenesulphonamido)cyclohexano[1,2-b]indoles has been found, which is characterized in that enantiomerically pure cyclohexano[1,2-b]indolamines of the general formula (XX)

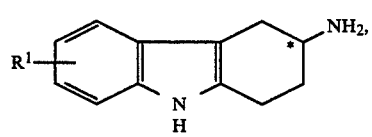

(XX)

in which

R$^1$ has the indicated meaning, are reacted with sulphonyl halides of the general formula (XVII)

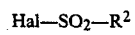 (XVII), in which

R$^2$ has the indicated meaning, and

Hal represents fluorine, chlorine, bromine or iodine, preferably chlorine or bromine, in the presence of inert solvents and, where appropriate, in the presence of a base.

Suitable solvents for the process are the customary organic solvents which do not change under the reaction conditions. These preferably include ethers such as diethyl ether, dioxane, tetrahydrofuran or glycol dimethyl ether, or hydrocarbons, such as benzene, toluene, xylene, hexane, cyclohexane or petroleum fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is equally possible to use mixtures of the said solvents.

Bases for the process can be customary basis compounds. These preferably include alkali metal or alkaline earth metal hydroxides, such as lithium hydroxide, sodium hydroxide, potassium hydroxide or barium hydroxide, or alkali metal hydrides such as sodium hydride, or alkali metal or alkaline earth metal carbonates such as sodium carbonate, sodium bicarbonate, potassium carbonate or calcium carbonate, or alkali metal alcoholates such as, for example, sodium methanolate, sodium ethanolate, potassium methanolate, potassium ethanolate or potassium tert.-butylate, or alkali metal amides such as lithium diisopropylamide or sodamide, or organic amines such as ethyldiisopropylamine, benzyltrimethylammonium hydroxide, tetrabutylammonium hydroxide, pyridine, dimetylaminopyridine, triethylamine, N-methylpiperidine, 1,5-diazabicyclo[4.3.0]non-5-ene or 1,5-diazabicyclo[5.4.0]undec-5-ene.

The process according to the invention is generally carried out in a temperature range of from $-30°$ C. to $+150°$ C., preferably from $-20°$ C. to $+80°$ C.

The process according to the invention is generally carried out under atmospheric pressure. It is equally possible to carry it out under reduced pressure or under elevated pressure (for example in a range from 0.5 to 200 bar).

The enantiomerically pure cyclohexano[1,2-b]indolamines of the general formula (XX) according to the invention are new and can be prepared by the following synthetic routes A, B or C.

Synthetic route A

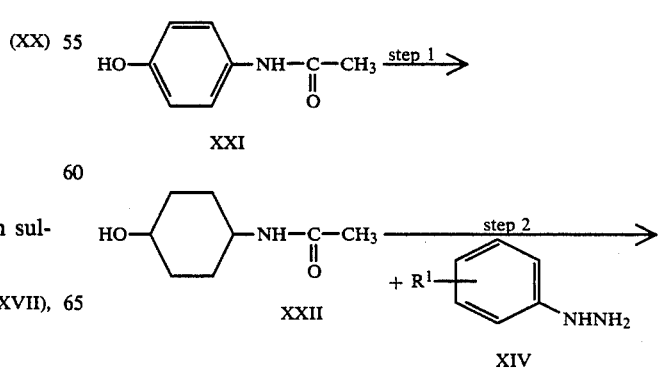

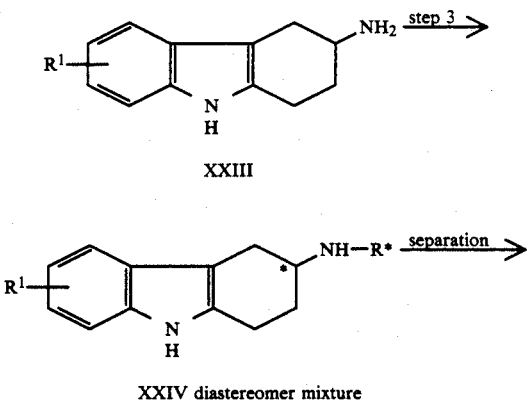

XXIII

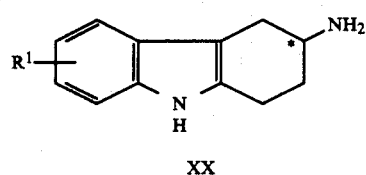

XXIV diastereomer mixture individual diastereomers —step 4→

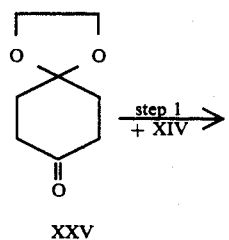

XX

R¹ has the indicated meaning, and

R* represents an enantiomerically pure D-, or L-amino acid residue, preferably the 2S-(chloroacetamido)-3-phenylpropionyl radical.

Synthetic route B

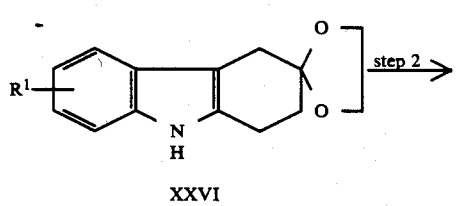

XXV

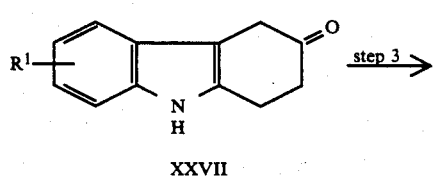

XXVI

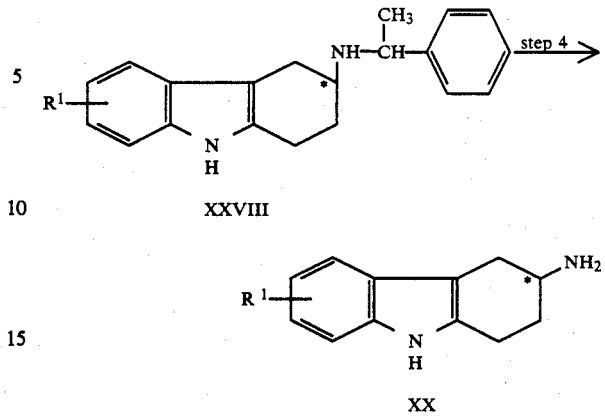

XXVIII

XX

R¹ has the indicated meaning.

Synthetic route A

According to this, in step 1 paracetamol (XXI) is hydrogenated on Raney nickel to give a cis/trans mixture of 4-acetamidocyclohexanol (XXII) as described by Billman, J. H., Bühler, J. A. in J. Am. Chem. Soc. 75, 1345 (1953).

In step 2 4-acetamidocyclohexanol (XXII) is subjected in a one-pot process after an oxidation with $CrO_3$ to a Fisher indole synthesis with phenylhydrazines (XIV), and then the acetyl group is removed by acid hydrolysis.

This process step is carried out in solvents such as water, acetic acid and/or propionic acid, at temperatures from 0° C., to +150° C., preferably from 0° C. to 110° C. The racemic 3-amino-1,2,3,4-tetrahydrocarbazoles (XXIII) which are readily accessible in this way are converted in step 3 by coupling with derivatives of enantiomerically pure amino acids, where appropriate in their activated form, into the corresponding diastereomer mixtures which can be separated into the individual diastereomers by customary methods such as crystallization or column chromatography.

Enantiomerically pure amino acid derivatives which are suitable and preferred are acetylphenylalanine, N-tert-butoxycarbonylphenylalanine, chloroacetylphenylalanine, carbo-benzoxyphenylalanine, methoxy-phenylacetic acid or acetoxy-phenylacetic acid, preferably N-chloroacetyl-N-phenyl-alanine.

The activating agents which are generally used are the customary peptide-coupling reagents. These preferably include carbodiimides such as, for example, diisopropylcarbodiimide, dicyclohexylcarbodiimide or N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium 3-sulphonate, or propanephosphonic anhydride, or isobutyl chloroformate, or benzotriazolyloxy-tris(dimethylamino)phosphonium hexafluorophosphate, or methanesulphonyl chloride, where appropriate in the presence of bases such as triethylamine or N-ethylmorpholine or N-methylpiperidine, or dicyclohexylcarbodiimide and N-hydroxysuccinimide.

The coupling is generally carried out in inert organic solvents, preferably in chlorinated hydrocarbons such as methylene chloride or chloroform, or hydrocarbons such as benzene, toluene, xylene or petroleum fractions,

XXVII or in ethers such as dioxane, tetrahydrofuran or diethyl ether, or in ethyl acetate, dimethylformamide, dimethyl sulphoxide or acetone, acetonitrile or nitromethane, at temperatures from −80° C. to +50° C., preferably from −40° C. to +30° C.

After separation of the diastereomer mixtures (XXIV), in step 4 the individual diastereomers are subjected to acid hydrolysis to give the enantiomerically pure amines (XX).

The hydrolysis is generally carried out with inorganic or organic acids such as hydrochloric acid, hydrobromic acid, sulphuric acid, phosphoric acid, formic acid, acetic acid, propionic acid, methanesulphonic acid or trifluoroacetic acid, or mixtures of the said acids.

The solvents which are generally used for this are water or the aqueous solution of the corresponding acid or mixture of acids which is used.

The hydrolysis is generally carried out in a temperature range from +20° C. to +150° C., preferably from +20° C. to +120° C.

The process according to the invention is generally carried out under atmospheric pressure. It is equally possible to carry it out under reduced or under elevated pressure, for example in an autoclave or pressure tube. It has proved advantageous in this to add thioglycolic acid to the reaction mixture as oxidation inhibitor.

Synthetic route B

According to this, 1,4-cyclohexanedione monoethylene ketal (XXV) is reacted with phenylhydrazines (XIV) in a Fischer indole synthesis to give ketals (XXVI) as described by A. Britten and G. Lockwood in J. Chem. Soc., Perkin Trans. 1, 1974, 1824–1827.

Hydrolysis of the ketals (XXVI) in step 2 gives the ketones (XXVII) which, in step 3, are converted by reductive amination with S-phenethylamine into the diastereomer mixtures (XXVIII).

The reductive amination is generally carried out with reducing agents such as hydrogen, where appropriate in the presence of palladium, platinum, or palladium on animal charcoal as catalyst, or complex hydrides, preferably sodium borohydride, potassium borohydride, lithium borohydride, zinc borohydride, lithium aluminium borohydride, aluminum hydride; di-iso-butyl-aluminum-hydride, lithium triethylhydridoborate, sodium cyanotrihydridoborate, tetrabutylammonium cyanotrihydridoborate, tetrabutylammonium hydridoborate, lithium aluminum hydride, sodium bis[2-methoxyethoxy]dihydridoaluminate or lithium hydrido-tris[1-methylpropyl]borate in inert solvents such as hydrocarbons, preferably benzene, toluene or xylene, or chlorinated hydrocarbons such as methylene chloride or chloroform, or ethers such as diethyl ether, tetrahydrofuran, dioxane or 1,2-dimethoxymethane, or acetonitrile, dimethylformamide, dimethyl sulphoxide or alcohols such as methanol, ethanol, propanol or isopropanol, in a temperature range from −80° C. to +100° C., preferably −80° C. to +50° C.

The diastereomer mixture (XXVIII) is separated into the individual diastereomers by customary methods such as chromatography or crystallization, preferably by crystallization, where appropriate in the form of suitable acid addition products.

Suitable acid addition products in this context are addition products of the enantiomers according to the invention with inorganic or organic acids. These preferably include hydrochloric acid, sulphuric acid, phosphoric acid or methanesulphonic acid, benzenesulphonic acid, naphthalenedisulphonic acid or acetic acid, maleic acid, fumaric acid, citric acid or lactic acid.

The removal of the phenylethyl groups in the separated diastereomers (XXVIII) is carried out in step 4 by catalytic transfer hydrogenation to give the enantiomerically pure amines (XX).

Step 4 is generally carried out with reducing agents such as hydrogen, where appropriate in the presence of palladium, palladium on animal charcoal, or platinum, or ammonium formate, in water or organic solvents such as alcohols, for example methanol, ethanol, propanol or isopropanol, or dimethylformamide or dimethyl sulphoxide or mixtures thereof, in a temperature range from 0° C. to +200° C., preferably from +20° C. to +150° C. (L. E. Overman and S. Sugai, J. Org. Chem. 50, 4154–4155 (1985).

Synthetic route C

According to this, racemate resolution of the compounds (XXIII) is carried out by salt formation with optically active acids and crystallization of these salts, once or several times, from suitable solvents. The enantiomerically pure compounds (XXIII) are liberated, by treatment with bases, from the salts which have thus been obtained.

Suitable optically active acids are: (+)-camphorsulphonic acid, (−)-camphorsulphonic acid, (+)-camphor-3-carboxylic acid, (−)-camphor-3-carboxylic acid, (+)-camphoric acid, (−)-camphoric acid, (+)-malic acid, (−)-malic acid, (+)-mandelic acid, (−)-mandelic acid, (+)-lactic acid, (−)-lactic acid, (+)-2-[(phenylamino)carbonyloxy]-propionic acid, (−)-2-[(phenylamino)carbonyloxy]-propionic acid, (−)-αmethoxyphenylacetic acid, (−)-di-O-benzoyltartaric acid, (−)-di-O-4-toluoyltartaric acid, (−)-methoxyacetic acid, (−)-1,1'-binaphthyl-2,2'-diyl-hydrogen phosphate.

Suitable solvents for the crystallization are solvents such as water, alcohols such as methanol, ethanol, isopropanol, n-propanol, n-butanol, sec-butanol or tert-butanol, ethers such as diethyl ether, tetrahydrofuran, dioxane or glycol dimethyl ether, ketones such as acetone, methyl ethyl ketone or methyl isobutyl ketone, hydrocarbons such as benzene, toluene, xylene, hexane or cyclohexane, chlorinated hydrocarbons such as dichloromethane or chloroform, or ethyl acetate, acetonitrile, nitromethane, dimethyl sulphoxide, dimethylformamide or sulpholane. It is equally possible to use mixtures of the said solvents.

Possible bases for the process are the customary basic compounds. These preferably include alkali metal or alkaline earth metal hydroxides such as lithium hydroxide, sodium hydroxide, potassium hydroxide or barium hydroxide, or alkali metal hydrides such as sodium hydride, or alkali metal or alkaline earth metal carbonates such as sodium carbonate, sodium bicarbonate, potassium carbonate or calcium carbonate, or alkali metal alcoholates such as, for example, sodium methanolate, sodium ethanolate, potassium methanolate, potassium ethanolate or potassium tert.-butylate.

The new cycloalkano[1,2-b]indole-sulphonamides and their salts can be used as active compounds in medicaments. The active compounds exhibit an action inhibiting platelet aggregation and antagonizing thromboxane $A_2$. They can preferably be used for the treatment of thromboses, thromboembolisms, ischaemias, and as antiasthmatics and as anti-allergics. The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compound should in each case be present in a concentration of about 0.5 to 90% by weight, preferably 5 to 70% by weight, which suffices to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration can be effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavour-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is generally about 0.01 to 20 mg/kg, preferably 0.1 to 10 mg/kg, of body weight.

Nevertheless, it can at times be advantageous to deviate from the amounts mentioned, and in particular to do so as a function of the body weight or of the nature of the administration method, but also as a function of individual behaviour towards the medicament, or the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day.

The cycloalkano[1,2-b]indole-sulphonamides according to the invention can be used both in human medicine and in veterinary medicine.

Preparation examples

Example 1

3-(Nitromethyl)cyclopentanone

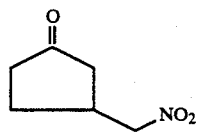

100 g of 2-cyclopentenone are dissolved together with 666 ml of nitromethane and 5 g of 1,5-diazabicyclo[4.3.0]non-5-ene (DBN) in 1.1 l of isopropanol, and the solution is left to stand at room temperature for 5 h. The isopropanol is then substantially distilled in vacuo, and the residue is dissolved in ethyl acetate and the solution is washed twice with 0.5 l of dilute sulphuric acid each time. The organic phase is dried with sodium sulphate and evaporated. In this way 154 g (88% of theory) of 3-(nitromethyl)cyclopentanone are obtained sufficiently pure for the next reaction.

$R_f = 0.52$ $CH_2Cl_2$: $CH_3OH = 99:1$

Example 2

3-(Aminomethyl)cyclopentanol

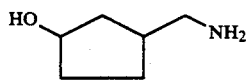

57.2 g (0.4 mol) of 3-(nitromethyl)cyclopentanone are dissolved, under nitrogen, in 573 ml of absolute tetrahydrofuran. At 0° C., 800 ml of a one-molar solution of lithium aluminum hydride in tetrahydrofuran are added dropwise to this solution. After the dropwise addition is complete, the mixture is stirred at 0° C. for 1 h. The cooling bath is then removed, whereupon the temperature of the reaction solution rises to 40° C. After the temperature has fallen to 20° C. the mixture is stirred at this temperature for 1 h. The reaction mixture is cooled to 0° C. and then 100 ml of 45% strength sodium hydroxide solution are cautiously added dropwise. After the dropwise addition is complete, the reaction mixture is stirred at room temperature for 1 h, filtered through kieselgur, and kieselgur is washed with 1.5 l of tetrahydrofuran. The combined filtrates are thoroughly evaporated in vacuo. In this way 22.5 g (49% of theory) of viscous oily product are obtained.

$R_f = 0.01$ $CH_2Cl_2$: $CH_3OH = 9:1$

Example 3

3-(Benzenesulphonamidomethyl)cyclopentanol

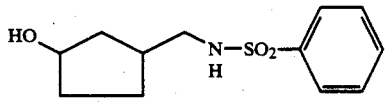

9 g (0.078 mol) of 3-(aminomethyl)cyclopentanol are dissolved together with 13.8 g=10 ml (0.078 mol) of triethylamine in 200 ml of tetrahydrofuran. Then, at 0°-5° C., 7.9 g=10.8 ml (0.078 mol) of benzenesulphonyl chloride are added dropwise. After the dropwise addition is complete, the mixture is stirred at 0° C. for 1 h. The reaction mixture is then diluted with 200 ml of methylene chloride, and washed twice with 150 ml of dilute sulphuric acid each. The organic phase is then extracted twice with 150 ml of 2N sodium hydroxide solution each time, the combined extracts are acidified with concentrated hydrochloric acid, and extracted twice with 150 ml of methylene chloride each time. The combined methylene chloride phases are dried with sodium sulphate and evaporated in vacuo. In this way 9.1 g (39% of theory) of viscous oily isomer mixture are obtained as the product.

$R_f$=0.51 and 0.45 CH$_2$Cl$_2$: CH$_3$OH=95:5

Example 4

3-(Benzenesulphonamidomethyl)cyclopentanone

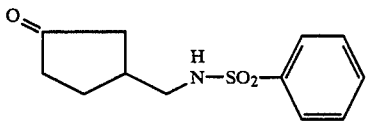

7.5 g (0.0294 mol) of 3-(benzenesulphonamidomethyl)cyclopentanol are dissolved in 60 ml of glacial acetic acid. At 0°-5° C. 2.79 g (0.0279 mol) of chromium trioxide dissolved in 2 ml of water and 8.8 ml of glacial acetic acid are added dropwise, and then the temperature of the reaction mixture is allowed to rise to room temperature. After the reaction mixture has been stirred at room temperature for 1 hour it is diluted with 200 ml of ether and washed twice with 150 ml of water each time. The organic phase is then extracted twice with 200 ml of 2N sodium hydroxide solution each time, and the combined sodium hydroxide phases are acidified with concentrated hydrochloric acid and extracted twice with 200 ml of methylene chloride each time. The combined methylene chloride phases are dried with sodium sulphate and evaporated in vacuo. In this way 4.4 g (59% of theory) of viscous oily product are obtained.

$R_f$=0.51 CH$_2$Cl$_2$: CH$_3$OH=95:5

Example 5

1-(Benzenesulphonamidomethyl)cyclopentano[1,2-b]indole

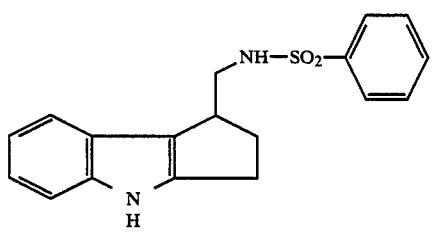

21 g (0.082 mol) of 3-(benzenesulphonamidomethyl)-cyclopentanone are dissolved together with 9 g (0.0826 mol) of phenylhydrazine in 200 ml of glacial acetic acid, and the solution is heated under reflux for 4 h. The reaction solution is then diluted with 1.3 l of ether, and 500 ml of water are added. While cooling and stirring, the mixture is made alkaline with 45% strength sodium hydroxide solution, and then the organic phase is separated off. The aqueous phase is extracted once more with 500 ml of ether, and the combined organic phases are dried with sodium sulphate and evaporated. The residue which is thus obtained is chromatographed on 2 kg of silica gel (Merck 0.04–0.063 mm) with a mixture of toluene and ethyl acetate in the ratio 85 to 15. In this way a fraction which, after evaporation, provides 1.9 g (7% of theory) of crystalline product is obtained, melting point: 161°-164° C. $R_f$=0.92 CH$_2$Cl$_2$: CH$_3$OH=95:5

Example 6

1-[N-(Benzenesulphonyl)-N-(2-cyanoethyl)aminomethyl]-4-(2-cyanoethyl)cyclopentano[1,2-b]indole

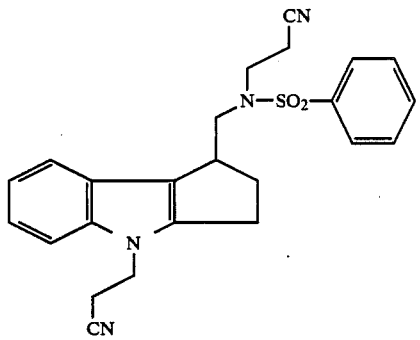

1.9 g (0.0058 mol) of 1-(benzenesulphonamidomethyl)cyclopentano[1,2-b]indole are stirred together with 1.83 g 20=2.3 ml (0.0346 mol) of acrylonitrile and 0.24 g (0.00058 mol) of a 40% strength solution of benzyltrimethylammonium hydroxide in methanol in 60 ml of dioxane at 60°-70° C. for 2 h. Then the reaction mixture is evaporated in vacuo, and the residue is taken up in methylene chloride and the solution is extracted twice with dilute sulphuric acid. The organic phase is washed with saturated bicarbonate solution, dried with sodium sulphate and evaporated. In this way 2.4 g (95% of theory) of product are obtained as a solid foam. $R_f$=0.45 CH$_2$Cl$_2$: CH$_3$OH=99:1

Example 7

1-(Benzenesulphonamidomethyl)-4-(2-carboxyethyl)-cyclopentano[1,2-b]indole

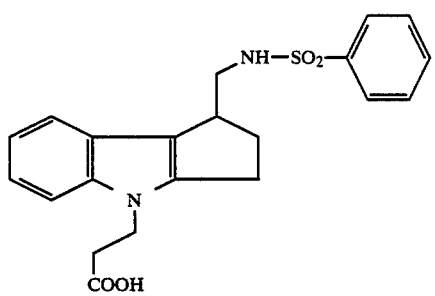

2.4 g (0.0055 mol) of 1-[N-(benzenesulphonyl)-N-(2-cyanoethyl)aminomethyl]-4-(2-cyanoethyl)cyclopentano[1,2-b]indole are dissolved in 35 ml of isopropanol, and 55 ml of a 10% strength potassium hydroxide solution are added. The reaction mixture is stirred at 70° C. for 4 h, then diluted with 100 ml of water and extracted with 100 ml of methylene chloride. The aqueous phase is acidified with dilute sulphuric acid and extracted 3 times with 100 ml of methylene chloride each time. The combined organic phases are dried with sodium sulphate and evaporated. The oily residue (1.9 g) is dissolved in methanol, and 0.26 g of sodium methylate is added. Evaporation of this solution provides 2.0 g (69.2% of theory) of the product as a microcrystalline sodium salt. R$_f$=0.37 CH$_2$Cl$_2$: CH$_3$OH=95:5

Example 8

3-(4-Fluorophenylsulphonamidomethyl)cyclopentanol

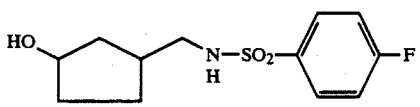

In analogy to the the procedure for Example 3, 19.8 g (0.172 mol) of 3-(aminomethyl)cyclopentanol are reacted with 28.3 g (0.172 mol) of 4-fluorophenylsulphonamide. This results in 17.3 g (36% of theory) of viscous oily isomer mixture being obtained as the product. R$_f$=0.53 and 0.46 CH$_2$Cl$_2$: CH$_3$OH=95:5

Example 9

3-(4-Fluorophenylsulphonamidomethyl)cyclopentanone

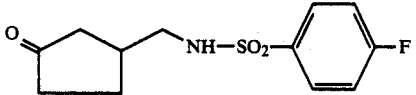

In analogy to the procedure for Example 4, 17.3 g (0.0638 mol) of 3-(4-fluorophenylsulphonamidomethyl)cyclopentanol were oxidized. This results in 14.3 g (83% of theory) of viscous oily product being obtained. R$_f$=0.76 CH$_2$Cl$_2$: CH$_3$OH=9:1

Example 10

1-(4-Fluorophenylsulphonamidomethyl)cyclopentano[1,2-b]-indole

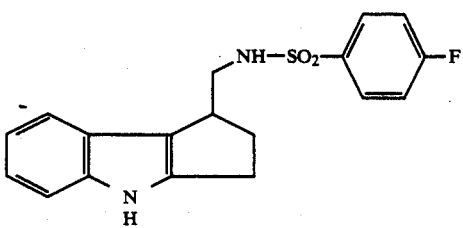

14.3 Lg (0.0527 mol) of 3-(4-fluorophenylsulphonamidomethyl)cyclopentanone were reacted with phenylhydrazine in analogy to Example 5. In this way, after chromatography on silica gel, 0.67 g (3.7% of theory) of microcrystalline product is obtained. R$_f$=0.47 CH$_2$Cl$_2$: CH$_3$OH=99:1

Example 11

4-(2-Cyanoethyl)-1-[N-(4-fluorophenylsulphonyl)-N-(2-cyanoethyl)aminomethyl]cyclopentano[1,2-b]indole

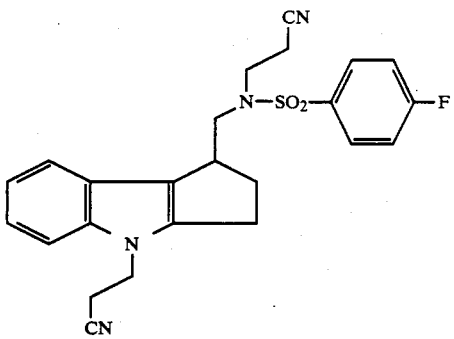

0.67 g (0.00195 mol) of 1-(4-fluorophenylsulphonamidomethyl)cyclopentano[1,2-b]indole were reacted in analogy to Example 6. In this way 0.83 g (95% of the theory) of product is obtained as a solid foam. R$_f$=0.39 toluene: ethyl acetate=8:2

Example 12

4-(2-Carboxyethyl)-1-(4-fluorophenylsulphonamidomethyl)cyclopentano[1,2-b]indole

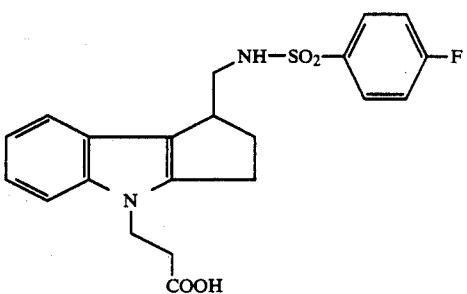

0.83 g (0.00184 mol) of 4-(2-cyanoethyl)-1-[N-(4-fluorophenylsulphonyl)-N-(2-cyanoethyl)aminomethyl]cyclopentano[1,2-b]indole is hydrolyzed in analogy to Example 7. In this way 0.67 g (87% of theory) of crystalline product is obtained as the sodium salt, melting point: 150°–160° C. R$_f$=0.59 CH$_2$Cl$_2$: CH$_3$OH=9:1

Example 13

3-(4-Chlorophenylsulphonamidomethyl)cyclopentanol

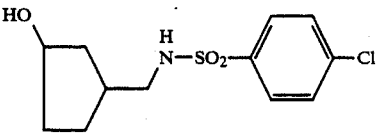

16.8 g (0.146 mol) of 3-(aminomethyl)cyclopentanol are reacted with 4-chlorophenylsulphonyl chloride in analogy to Example 3. In this way 16.6 g (39% of theory) of viscous oily product are obtained as an isomer mixture. R$_f$=0.46 and 0.44 CH$_2$Cl$_2$: CH$_3$OH=95:5

Example 14

3-(4-Chlorophenylsulphonamidomethyl)cyclopentanone

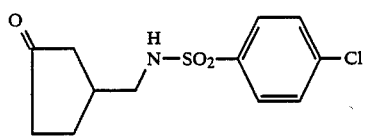

16.6 g (0.0573 mol) of 3-(4-chlorophenylsulphonamidomethyl)cyclopentanol are oxidized in analogy to Example 4. In this way 13.8 g (83.7% of theory) of viscous oily product are obtained. $R_f=0.7$ CH$_2$Cl: CH$_3$OH=95:5

Example 15

1-(4-Chlorophenylsulphonamidomethyl)cyclopentano[1,2-b]-indole

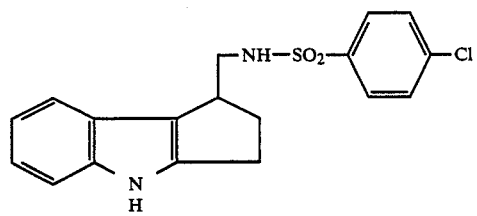

13.8 g (0.048 mol) of 3-(4-chlorophenylsulphonamidomethyl)cyclopentanone are reacted with phenylhydrazine in analogy to Example 5. In this way, after chromatography on silica gel, 1.65 g (9.5% of theory) of product are obtained as a solid foam.

$R_f=0.46$ CH$_2$Cl$_2$: CH$_3$OH=99:1

Example 16

1-[N-(2-Chlorophenylsulphonyl)-N-(2-cyanoethyl)aminomethyl]-4-(2-cyanoethyl)cyclopentano[1,2-b]indole

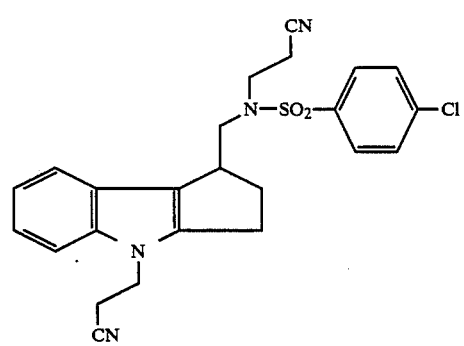

1.65 g (0.0046 mol) of 1-(4-chlorophenylsulphonamidomethyl)cyclopentano[1,2-b]indole are reacted in analogy to Example 6. In this way 1.8 g (84% of theory) of product are obtained as a solid foam. $R_f=0.38$ toluene: ethyl acetate=8:2

Example 17

4-(2-Carboxyethyl)-1-(4-chlorophenylsulphonamidomethyl)cyclopentano[1,2-b]indole

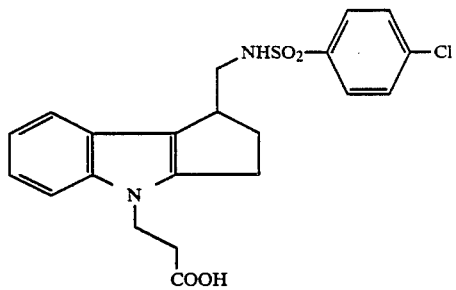

1.9 g (0.0038 mol) of 1-[N-(4-chlorophenylsulphonyl-N-(2-cyanoethyl)amidomethyl]-4-(2-cyanoethyl)cyclopentano[1,2-b]indole are hydrolyzed in analogy to Example 7. In this way 1.33 g (81.3% of theory) of product are obtained as the crystalline sodium salt, melting point: 160° C. $R_f=0.55$ CH$_2$Cl$_2$: CH$_3$OH=9:1

Example 18

4-(Benzenesulphonamido)cyclohexanol

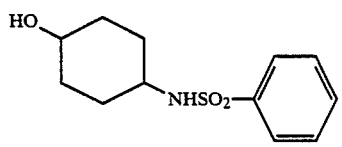

69 g (0.6 mol) of 4-aminocyclohexanol are reacted with 107 g (0.6 mol) of benzenesulphonyl chloride in analogy to Example 3. In this way 72.8 g (47% of theory) of crystalline product are obtained, melting point: 106°–108° C. $R_f=0.38$ CH$_2$Cl$_2$: CH$_3$OH=95:5

Example 19

4-(Benzenesulphonamido)cyclohexanone

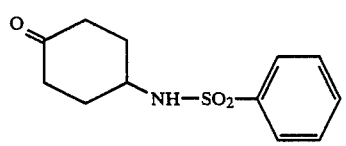

72.8 g (0.285 mol) of 4-(benzenesulphonamido)cyclohexanol are oxidized in analogy to Example 4. After crystallization from petroleum ether, 57.5 g (80% of theory) of product are obtained, melting point: 80°–82° C. $R_f=0.66$ CH$_2$Cl$_2$: CH$_3$OH=95:5

Example 20

3-(Benzenesulphonamido)-1,2,3,4-tetrahydrocarbazole

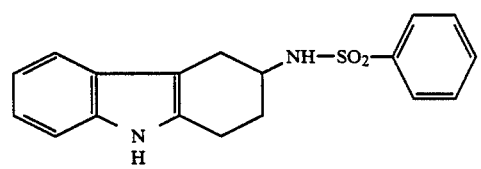

57.5 g (0.227 mol) of 4-(benzenesulphonamido)cyclohexanone are reacted with phenylhydrazine in analogy to Example 5. In this way 41.5 g (56% of theory) of product crystallized from isopropanol are obtained, melting point: 155° C. $R_f=0.82$ $CH_2Cl_2$: $CH_3OH=95:5$

Example 21

3-[N-(Benzenesulphonyl)-N-(2-cyanoethyl)amino]-9-(2-cyanoethyl)-1,2,3,4-tetrahydrocarbazole

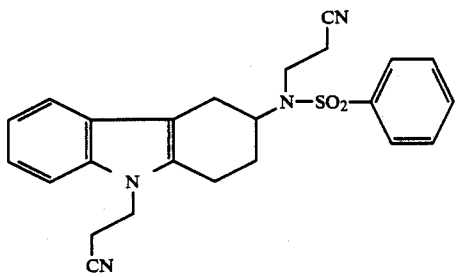

10 g (0.0306 mol) of 3-(benzenesulphonamido)-1,2,3,4-tetrahydrocarbazole are reacted in analogy to Example 6. In this way 10 g (75% of theory) of product crystallized from ether are obtained, melting point: 180°-190° C. $R_f=0.29$ toluene: ethyl acetate=8:2

Example 22

3-(Benzenesulphonamido)-9-(2-carboxyethyl)-1,2,3,4-tetrahydrocarbazole

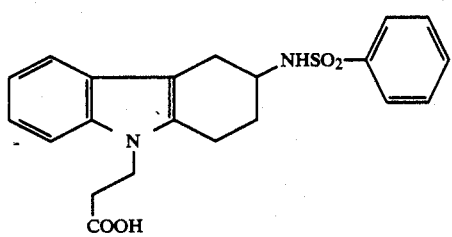

10 g (0.0263 mol) of 3-[N-(benzenesulphonyl)-N-(2-cyanoethyl)amino]-9-(2-cyanoethyl)-1,2,3,4-tetrahydrocarbazole are hydrolyzed in analogy to Example 7. In this way 7.57 g (68% of theory) of crystalline product are obtained as the sodium salt, melting point: 160°-165° C. $R_f=0.44$ $CH_2Cl_2$: $CH_3OH=95:5$ In analogy to Example 18, the following compounds listed in Table 1 were prepared:

TABLE 1

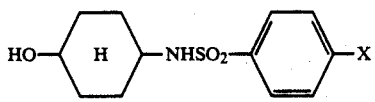

| Example No. | X | Yield | Rf | |
|---|---|---|---|---|
| 23 | Cl | 80% | 0.37 | $CH_2Cl_2$:$CH_3OH = 95:5$ |
| 28 | F | 75% | 0.4 | $CH_2Cl_2$:$CH_3OH = 95:5$ |
| 33 | $CH_3$ | 48.7% | 0.5 | $CH_2Cl_2$:$CH_3OH = 95:5$ |

In analogy to Example 19, the following compounds listed in Table 2 were prepared:

TABLE 2

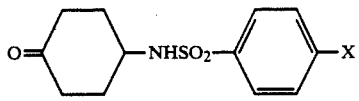

| Example No. | X | Yield | Rf | | Melting point: |
|---|---|---|---|---|---|
| 24 | Cl | 86% | 0.77 | $CH_2Cl_2$:$CH_3OH = 9:1$ | 103°-4° C. from petroleum ether |
| 29 | F | 94% | 0.7 | $CH_2Cl_2$:$CH_3OH = 9:1$ | 104°-8° C. from petroleum ether |
| 34 | $CH_3$ | 90.7% | 0.57 | $CH_2Cl_2$:$CH_3OH = 95:5$ | |

In analogy to Example 20, the following compounds listed in Table 3 were prepared:

TABLE 3

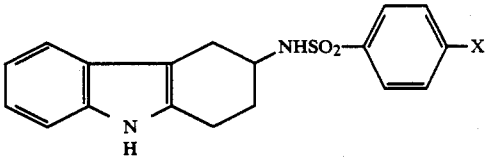

| Example No. | X | Yield | Rf | | Melting point: |
|---|---|---|---|---|---|
| 25 | Cl | 75.4% | 0.52 | toluene:ethyl acetate 8:2 | 163° C. from ether |
| 30 | F | 73% | 0.39 | $CH_2Cl_2$:$CH_3OH = 99:1$ | 146°-9° C. from ether |
| 35 | $CH_3$ | 55% | 0.42 | $CH_2Cl_2$:$CH_3OH = 8:2$ | 136°-8° C. from isopropanol |

In analogy to Example 21, the following compounds listed in Table 4 were prepared:

TABLE 4

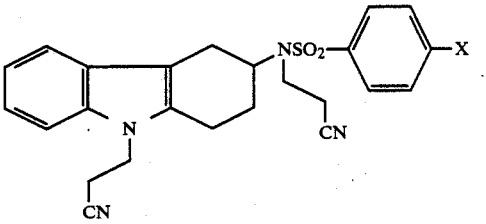

| Example No. | X | Yield | Rf | | Melting point: |
|---|---|---|---|---|---|
| 26 | Cl | 47% | 0.35 | toluene:ethyl acetate 8:2 | 204°-6° C. from ether/isopropanol |
| 31 | F | 53% | 0.29 | toluene:ethyl acetate 8:2 | 206°-8° C. from ether/isopropanol |
| 36 | $CH_3$ | 85% | 0.37 | toluene:ethyl acetate 8:2 | 180°-90° C. from ether |

In analogy to Example 22, the following compounds listed in Table 5 were prepared:

TABLE 5

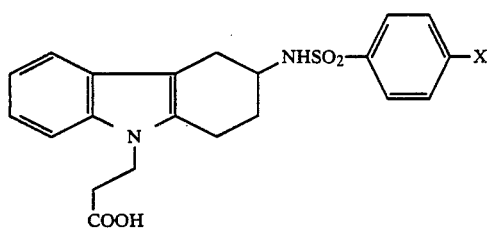

| Example No. | X | Yield | Rf | | Melting point: |
|---|---|---|---|---|---|
| 27 | Cl | 89.5% | 0.61 | CH$_2$Cl$_2$:CH$_3$OH = 9:1 | 150° C. Na salt |
| 32 | F | 98.5% | 0.57 | CH$_2$Cl$_2$:CH$_3$OH = 9:1 | 160°–70° C. Na salt |
| 37 | CH$_3$ | 95% | 0.53 | CH$_2$Cl$_2$:CH$_3$OH = 9:1 | 150°–60° C. Na salt |

Examples 38 and 39

3-r-(4-Fluorophenylsulphonamido)-9-(2-carboxyethyl)-1,2,3,4,4a-t,9a-t-hexahydrocarbazole (isomer A) and 3-r-(4-fluorophenylsulphonamido)-9-(2-carboxyethyl)-1,2,3,4,4a-c,9a-c-hexahydrocarbazole (isomer B)

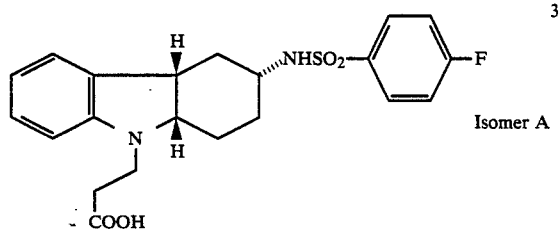

Isomer A

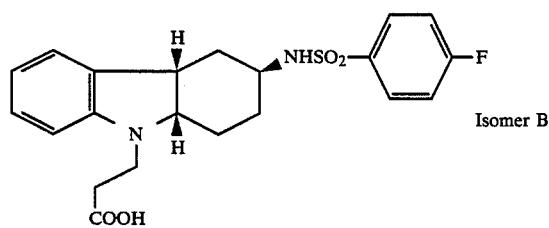

Isomer B 5 g (0.0114 mol) of 3-(4-fluorophenylsulphonamido)-9-(2-carboxyethyl)-1,2,3,4-tetrahydrocarbazole sodium salt are dissolved in 50 ml of trifluoroacetic acid and, at 0° C, 5.01 g (0.08 mol) of sodium cyanoborohydride are added in portions. The reaction mixture is allowed to reach room temperature, diluted with water and extracted with 200 ml of ethyl acetate. The ethyl acetate phase is extracted twice with each 100 ml of 2N sodium hydroxide solution, the combined sodium hydroxide phases are adjusted to pH 5, and extracted three times with each 150 ml of methylene chloride, dried with sodium sulphate and thoroughly evaporated in vacuo. The residue is chromatographed on 500 g of silica gel (Merck, 0.040–0.063 mm) with a 100 to 1 mixture of methylene chloride and glacial acetic acid. Two fractions are obtained in this way and, after evaporation, provide 2.87 g (60.2% of theory) of isomer (A) and 0.7 g (14.9% of theory) of isomer (B) respectively as a solid foam.

R$_f$ of isomer (A): 0.24; CH$_2$Cl$_2$: CH$_3$COOH = 100:2

R$_f$ of isomer (B): 0.14

Examples 40 and 41

3-r-(Benzenesulphonamido)-9-(2-carboxyethyl)-1,2,3,4,4a-t,9a-t-hexahydrocarbazole (isomer A) and 3-r-(benzenesulphonamido)-9-(2-carboxyethyl)-1,2,3,4,4a-c,9a-c-hexahydrocarbazole (isomer B)

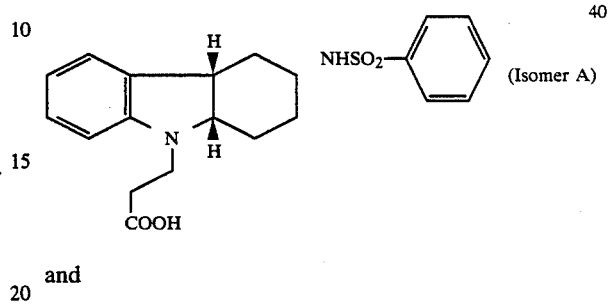

(Isomer A)

and (Isomer B)

1.18 g (0.0028 mol) of 3-(benzenesulphonamido)-9-(2-carboxymethyl)-1,2,3,4-tetrahydrocarbazole sodium salt are reduced in analogy to Example 38. Chromatography results in two fractions which, after evaporation, provide 0.45 g (40% of theory) of isomer A and 0.2 g (18% of theory) of isomer B as a solid foam.

R$_f$ of isomer A: 0.4; CH$_2$Cl$_2$:CH$_3$COOH = 100:4
R$_f$ of isomer B: 0.22

Example 42 and Example 43

3-r-(4-Methylphenylsulphonamido)-9-(2-carboxyethyl)-1,2,3,4,4a-t;9a-t-hexahydrocarbazole (isomer A)

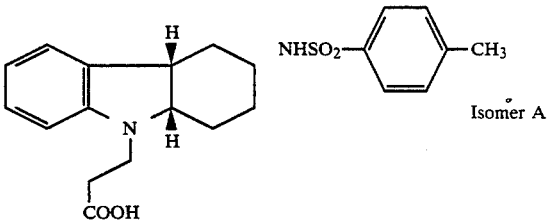

Isomer A and 3-r-(4-methylphenylsulphonamido)-9-(2-carboxyethyl)-1,2,3,4,4a-c,9a-c-hexahydrocarbazole (isomer B)

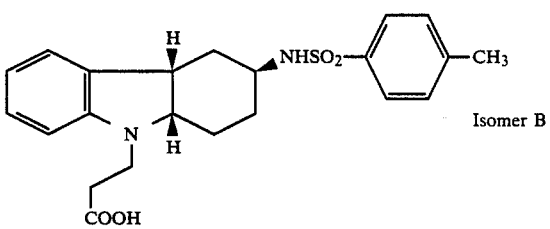

Isomer B 18.06 g of 3-(4-methylphenylsulphonamido)-9-(2-carboxyethyl)-1,2,3,4-tetrahydrocarbazole sodium salt are reduced in analogy to Example 38. Chromatography results in two fractions which, after evaporation, provide 3.65 g (20% of theory) of isomer A as a crystalline residue, melting point: 156°-62° C., and 1.11 g (6% of theory) of isomer B as a solid foam.

$R_f$ of isomer A: 0.39
$R_f$ of isomer B: 0.20
$CH_2Cl_2:CH_3COOH=100:2$

Example 44

3-(4-Chlorophenylsulphonamido)-6-fluoro-1,2,3,4-tetrahydrocarbazole

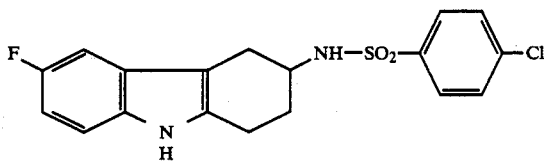

26.5 g of 4-(4-chlorophenylsulphonamido)cyclohexanone are reacted with 4-fluorophenylhydrazine in analogy to Example 5. This results in 35.4 g (100% of theory) of product being obtained as a solid foam. $R_f=0.53$ toluene:ethyl acetate=8:2

Example 45

3-[N-(4-Chlorophenylsulphonyl)-N-(2-cyanoethyl)amino]-9-(2-cyanoethyl)-6-fluoro-1,2,3,4-tetrahydrocarbazole

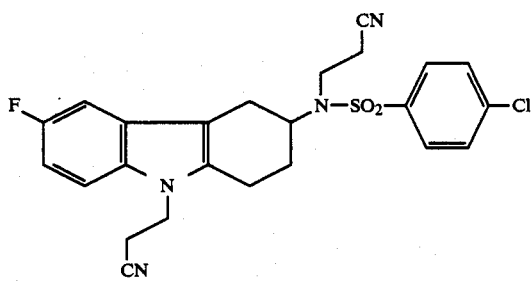

3.4 g of 4-(4-chlorophenylsulphonamido)-6-fluoro-1,2,3,4-tetrahydrocarbazole are reacted in analogy to Example 6. In this way 27.6 g (61% of theory) of product are obtained as a solid foam.

$R_f=0.25$ toluene:ethyl acetate=8:2

Example 46

3-(4-Chlorophenylsulphonamido)-9-(2-carboxyethyl)-6-fluoro-1,2,3,4-tetrahydrocarbazole

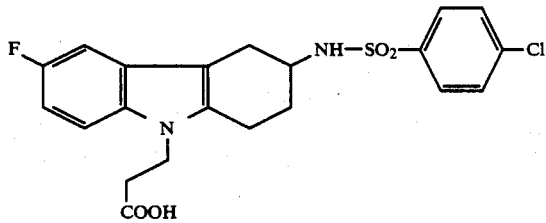

27.6 g of 3-[N-(chlorophenylsulphonyl)-N-(2-cyanoethyl)amino]-9-(2-cyanoethyl)-6-fluoro-1,2,3,4-tetrahydrocarbazole are hydrolyzed in analogy to Example 7.

In this way 25.6 g (100% of theory) of crystalline product are obtained, melting point: 118°-130° C. $R_f=0.52$ $CH_2Cl_2:CH_3OH=9:1$

Example 47

3-(Nitromethyl)cyclohexanone

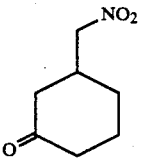

21.9 g of cyclohexanone are left to stand together with 175 ml of nitromethane and 2.1 g of 5-diazabicyclo[4.3.0.]non-5-ene (DBN) in 250 ml of isopropanol at room temperature for 2 days. The working up is carried out in analogy to the procedure for Example 1 and provides 37.2 g (100% of theory) of 3-(nitromethyl)cyclohexanone which is pure enough for the next reaction. $R_f=0.62$ $CH_2Cl_2:CH_3OH=99:1$

Example 48

3-(Aminomethyl)cyclohexanol

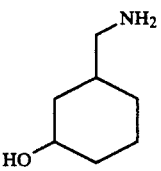

37.2 g of 3-(nitromethyl)cyclohexanone are reduced with lithium aluminum hydride in analog to the procedure for Example 2. In this way 7.5 g (24.5% of theory) of viscous oily 3-(aminomethyl)cyclohexanol are obtained. $R_f=0.04$ $CH_2Cl_2:CH_3OH=9:1$

Example 49

3-(4-Fluorophenylsulphonamidomethyl)cyclohexanol

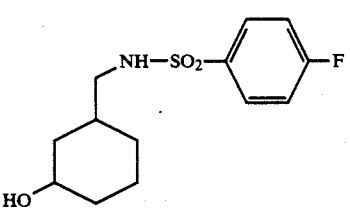

In analogy to the procedure for Example 3 7.5 g of 3-(aminomethyl)cyclohexanol are reacted with 11.3 g of 4-fluorophenylsulphonamide. This results in 11.05 g (66% of theory) of viscous oily isomer mixture being obtained as the product.

$R_f=0.41$ and 0.38 $CH_2Cl_2:CH_3OH=95:5$

Example 50

3-(4-Fluorophenylsulphonamidomethyl)cyclohexanone

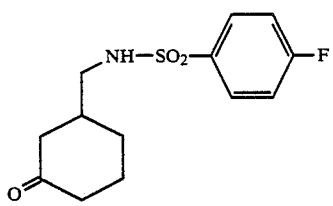

In analogy to procedure for Example 4, 11 g of 3-(4-fluorophenylsulphonamidomethyl)cyclohexanol are oxidized with chromium trioxide. This results in 9.3 g (86% of theory) of product being obtained as a solid foam. $R_f = 0.86$ $CH_2Cl_2:CH_3OH = 9:1$

Example 51

4-(4-Fluorophenylsulphonamidomethyl)-1,2,3,4-tetrahydrocarbazole

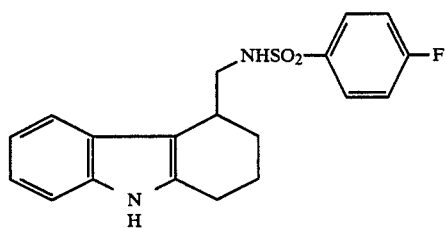

In analogy to the procedure for Example 5, 9 g of 3-(4-fluorophenylsulphonamidomethyl)cyclohexanone are reacted with phenylhydrazine. This results in 9 g of crude product which is chromatographed on 1 kg of silica gel (Merck 0.04–0.063 mm) in a mixture of toluene and ethyl acetate in the ratio 8 to 2. One fraction from this results, after evaporation, in 0.8 g (7.2% of theory) of product as a solid foam.

$R_f$: 0.44 toluene:ethyl acetate=8:2

Example 52

9-(2-Cyanoethyl)-4-[N-(4-fluorophenylsulphonyl)-N-(2-cyanoethyl)aminomethyl]-1,2,3,4-tetrahydrocarbazole

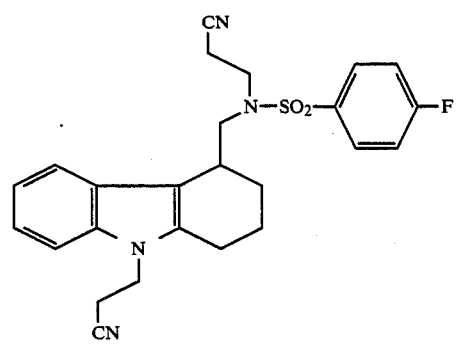

In analogy to the procedure for Example 6 0.8 g of 4-(4-fluorophenylsulphonamidomethyl)-1,2,3,4-tetrahydrocarbazole is reacted with acrylonitrile. This results in 0.91 g (88% of theory) of product being obtained as an oil. $R_f = 0.37$ toluene:ethyl acetate=8:2

Example 53

9-(2-Carboxyethyl)-4-(4-fluorophenylsulphonamidomethyl)-1,2,3,4-tetrahydrocarbazole

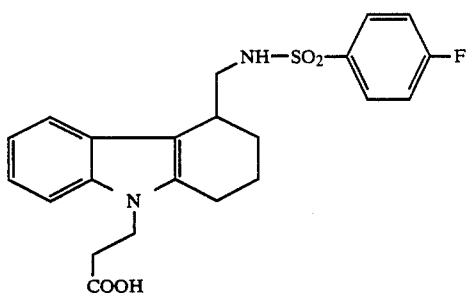

0.91 g of 9-(2-cyanoethyl)-4-[N-(4-fluorophenylsulphonyl)-N-(2-cyanoethyl)aminomethyl]-1,2,3,4-tetrahydrocarbazole is hydrolyzed in analogy to Example 7. In this way 0.77 g (89% of theory) of crystalline product is obtained as the sodium salt. Melting point: 160° C. $R_f = 0.57$ $CH_2Cl_2:CH_3OH = 9:1$

Example 54

4-N-Acetamidocyclohexanol

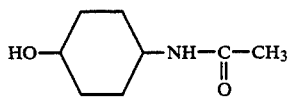

300 g of paracetamol in 750 ml of ethanol are hydrogenated on 30 g of Raney nickel at 180° C. and under 100 bar. After uptake of hydrogen is complete, the catalyst is removed by filtration and, after addition of 30 g of Raney nickel, hydrogenation is repeated at 180° C. and under 100 bar of excess pressure. The catalyst is then removed by filtration, the filtrate is evaporated in vacuo, and 200 ml of acetone are added to the still moist residue and stirred. After the crystals have been filtered off with suction, the mother liquor is concentrated further, the crystals which have separated out are once more filtered off with suction, and the mother liquor is again concentrated. The total obtained together with this 3rd batch is 342.4 g (80.8% of theory) of the product. Melting point: 100°–103° C.

Example 55

3-Amino-1,2,3,4-tetrahydrocarbazole (racemate)

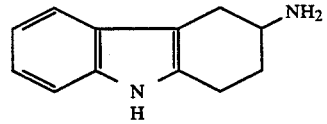

50 g (0.318 mol) of 4-N-acetamidocyclohexanol are dissolved in 400 ml of glacial acetic acid and, while stirring at room temperature, a solution of 31.8 g (0.318 mol) of chromium trioxide in a mixture of 26 ml of water and 105 ml of glacial acetic acid is added. This resulted in the temperature of the reaction solution rising to 60° C. The reaction mixture was stirred for 3 hours, and then 45.7 g (0.423 mol) of phenylhydrazine were added. This results in heating of the reaction solution to 80° C. and initial evolution of nitrogen. The reaction mixture is then heated under reflux for 2.5 hours. After the reaction mixture has been cooled, 500 ml of concentrated hydrochloric acid and 59 ml of thioglycolic acid are added and the mixture is heated under reflux, under nitrogen, for 16 hours. After cooling the mixture it is diluted with 500 ml of ethyl acetate and, while cooling, it is made alkaline with 45% strength sodium hydroxide solution. The precipitated chromium hydroxide is removed by filtration with suction through a layer of kieselguhr and is washed with a mixture of methylene chloride/methanol in the ratio 9:1. The organic phase is separated off from the filtrate, and the aqueous phase is extracted 3 more times with ethyl acetate. The combined organic phases are washed twice with 2N sodium hydroxide solution, and then extracted twice with 1 l of 2N sulphuric acid each time. The acidic aqueous phase is made alkaline with 45% strength sodium hydroxide solution and extracted 3 times with 1 l of methylene chloride each time. The combined methylene chloride phases are dried with sodium phosphate and evaporated. 300 ml of ether and 50 ml of isopropanol are added to the residue, and the mixture is stirred. The precipitated product is filtered off with suction, washed with ether and dried in vacuo. 28.6 g (48.3% of theory) of product are obtained. Melting point: 174°-176° C.

Example 56

3-[2S-(Chloroacetamido)-3-phenylpropionamido]-1,2,3,4-tetrahydrocarbazole (diastereomer mixture)

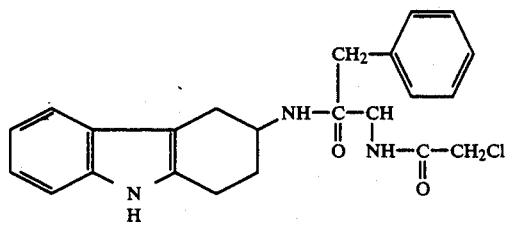

43 g (0.231 mol) of 3-amino-1,2,3,4-tetrahydrocarbazole and 55.87 g (0.231 mol) of N-chloroacetyl-L-phenylalanine are suspended in 1.5 l of methylene chloride under nitrogen and, at 0° C., 115.2 ml (0.832 mol) of triethylamine are added. Then, at −20° C., 150 ml (0.231 mol) of a 50% strength solution of propanephosphonic anhydride in methylene chloride are added dropwise to the reaction mixture. It is stirred at −20° C. for 30 minutes and then stirred at 0° C. for 1.5 hours. For working up, the reaction mixture is washed with 1 l of 2N sulphuric acid, with 1 l of water and twice with 1 l of saturated bicarbonate solution each time. After drying with sodium sulphate and evaporation, 100 g of solid residue are obtained.

Example 57 and Example 58

3-[2S-(Chloroacetamido)-3-phenylpropionamido]-1,2,3,4-tetrahydrocarbazole (diastereomer A and diastereomer B)

(a) Diastereomer separation by column chromatography 100 g of crude product from Example 56 are chromatographed on 2.5 kg of silica gel (0.063 to 0.2 mm, Merck) with a mixture of toluene/ethyl acetate in the ratio 6:4 as mobile phase. In this way 2 fractions are obtained, of which the first provides, after evaporation, 34 g (35.9% of theory) of diastereomer A (Example 57).
Melting point: 217°-220° C.
The second fraction provides, after evaporation, 24.3 g (25.7% of theory) of the other diastereomer B (Example 58).
Melting point: 193°-195° C.
Rotation of diastereomer A: $[\alpha]^{20} = 32.59°$ (CH$_3$OH)

(Example 57)

Rotation of diastereomer B: $[\alpha]^{20} = 5.09°$ (CH$_3$OH)

(Example 58)

(b) Diastereomer separation by crystallization 11.5 g of crude product from Example 56 are stirred in a mixture of ether and isopropanol. The crystals were filtered off with suction and heated under reflux in 40 ml of acetone for 3 hours. After cooling and leaving to stand overnight, the product was filtered off with suction and washed with acetone. In this way 1.2 g (5.5% of theory) of pure diastereomer A (Example 57) are obtained.

Example 59

3-Amino-1,2,3,4-tetrahydrocarbazole (enantiomer A)

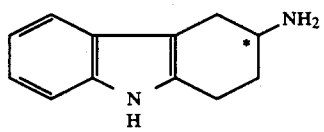

24.1 g (0.059 mol) of diastereomer 57 are dissolved in 460 ml of glacial acetic acid. 460 ml of concentrated hydrochloric acid and 24 ml of thioglycolic acid are added and heated under reflux, under nitrogen, for 3 days. The reaction mixture is then diluted with 200 ml of water and, while cooling, is adjusted to pH 5 with 45% strength sodium hydroxide solution. It is then extracted twice with 1.5 l of ethyl acetate each time, and the aqueous phase is then made alkaline with 45% strength sodium hydroxide solution and extracted 3 times with 1.5 l of ethyl acetate each time. The ethyl acetate extracts are combined, dried with sodium sulphate and evaporated. The residue is stirred in 150 ml of ether. The precipitated product is filtered off with suction and dried in vacuo. 7.8 g (71.3% of theory) of enantiomer A are obtained. Melting point: 160°-166° C. Rotation $[\alpha]^{20} = 78.38°$ (DMSO+10% water)

Example 60

3-Amino-1,2,3,4-tetrahydrocarbazole (enantiomer B)

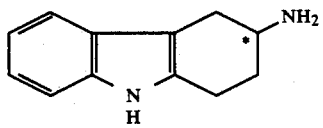

Enantiomer B is prepared by hydrolysis of 58 in analogy to the procedure for 59 from 57.
Melting point: 162°-167° C. Rotation $[\alpha]^{20} = -78.11°$ (DMSO+10% H$_2$O)

Example 61

3,3-Ethylenedioxy-1,2,3,4-tetrahydrocarbazole

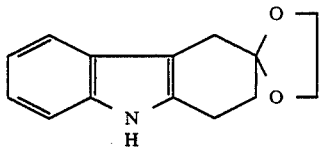

77.2 g (0.5 mol) of 1,4-cyclohexanedione monoethylene ketal are dissolved together with 48.4 ml (0.5 mol) of phenylhydrazine in 2 l of methylene chloride, and 300 g of magnesium sulphate are added, and the mixture is stirred for 30 min. The magnesium sulphate is then filtered off with suction, washed with methylene chloride, and the filtrate is evaporated. The residue is taken up in 1.5 l of benzene, and 62.1 g (0.46 mol) of anhydrous zinc chloride are added and the mixture is heated under reflux with a water separator for 3 h. The reaction solution is then concentrated, 2N sodium hydroxide solution is added, and the mixture is extracted 3 times with ethyl acetate. The combined ethyl acetate phases are dried with sodium sulphate and evaporated. The residue crystallizes from a little ether. In this way 3.5 g (72.9% of theory) of the product are obtained.

Melting point: 145°–146° C.

Example 62

1,2,4,9-Tetrahydrocarbazol-3-one

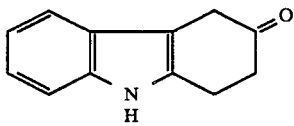

165 g (0.72 mol) of 3,3-ethylenedioxy-1,2,3,4-tetrahydrocarbazole are dissolved in 2 l of acetone, and 3 g of p-toluenesulphonic acid are added. After the reaction solution has been heated under reflux for 4 h it is concentrated, 2 l of ethyl acetate are added, and the mixture is extracted 3 times with 1 l of saturated bicarbonate solution each time. The organic phase is dried with sodium sulphate and evaporated. The residue crystallizes from ether. In this way 118.7 g (89.1% of theory) of the product are obtained.

Melting point: 145°–148° C.

Example 63

3-(1S-Phenylethylamino)-1,2,3,4-tetrahydrocarbazole

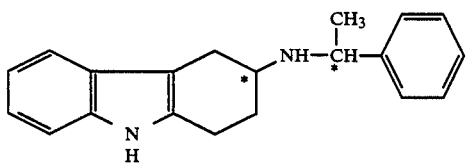

11.06 g (0.0595 mol) of 1,2,4,9-tetrahydrocarbazol-3-one are heated together with 7.78 g (0.065 mol) of 1S-phenylethylamine in 300 ml of benzene under reflux with a water separator for 1 h. After removal of the benzene by evaporation, the residue is dissolved in 50 ml of methylene chloride, and the solution is added dropwise to a solution of 15.3 g (0.0595 mol) of tetrabutylammonium borohydride in 120 ml of methylene chloride at −50° C. The reaction mixture is allowed to return to room temperature within 1 h, 6 ml of methanol are added, and 120 ml of 2N sulphuric acid are added cautiously (evolution of hydrogen). After stirring at room temperature for 1 h, the crystals which have separated out are filtered off with suction and washed twice with water and once with methylene chloride. After drying under high vacuum, 0.16 g (39.7% of theory) of the product is obtained as hydrogen sulphate.

Melting point: 160°–170° C.

Rotation: $[\alpha]^{20} = 26.36°$ (CH$_3$OH/H$_2$O = 80:20)

Example 64

3-Amino-1,2,3,4-tetrahydrocarbazole (enantiomer A)

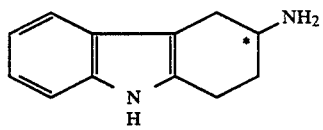

[Example 64, prepared by process B, is identical to Example 59]

10 g of the hydrogen sulphate obtained from Example 53 are, for conversion into the hydrochloride, suspended in 50 ml of methanol, and 30 ml of 2N sodium hydroxide solution are added, and the mixture is extracted with ethyl acetate. The organic phase is evaporated, and the residue is dissolved in 50 ml of methanol, and 20 ml of concentrated hydrochloric acid are added. The hydrochloride precipitates out on concentration in vacuo. After filtration with suction, washing with water and drying in vacuo, 7.6 g of hydrochloride are obtained. These 7.6 g (0.023 mol) of hydrochloride are heated together with 7.17 g (0.115 mol) of ammonium formate and 7.2 g of 10% palladium on active charcoal in 80 ml of dry dimethylformamide under reflux (under nitrogen) for 20 min. After cooling, the mixture is diluted with water, and the catalyst is filtered off with suction and washed with water. The combined filtrates are acidified with 2N sulphuric acid and extracted twice with ethyl acetate. The aqueous phase is made alkaline with 2N sodium hydroxide solution and extracted three times with ethyl acetate. The organic phases are dried with sodium sulphate and evaporated. The residue is further evaporated under high vacuum to remove dimethylformamide. 3 g (70% of theory) of crystalline enantiomer A are obtained from ether.

Melting point: 160°–166° C.

Rotation: $[\alpha]^{20} = 78.38°$ (DMSO+10% water)

Example 65

3-(4-Fluorophenylsulphonamido)-1,2,3,4-tetrahydrocarbazole (enantiomer A)

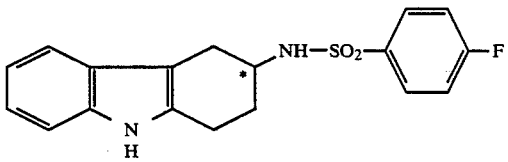

3.72 g (0.02 mol) of Example 59 are suspended together with 3 ml (0.022 mol) of triethylamine in 30 ml of methylene chloride and, while cooling, 3.9 g (0.02 mol) of 4-fluorobenzenesulphonyl chloride are added. The reaction mixture is dissolved at room temperature for 1 h and then stirred with 200 ml of ethyl acetate and extracted twice with 2N sulphuric acid and twice with 2N sodium hydroxide solution. The organic phase is dried with sodium sulphate and evaporated. Ether is added to the solid residue which is crystallized. 5.8 g (84% of theory) of the product are obtained.

Melting point: 150°-152° C.
Rotation: $[\alpha]^{20} = 50.43°$ (CHCl$_3$)

Example 66

3-(4-Fluorophenylsulphonamido)-1,2,3,4-tetrahydrocarbazole (enantiomer B)

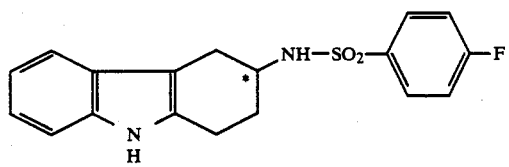

Enantiomer B is prepared from Example 60 in analogy to the preparation of Example 65 from Example 59.
Melting point: 150°-152° C.
Rotation: $[\alpha]^{20} = -48.99°$ (CHCl$_3$)

Example 67

3-[N-(4-Fluorophenylsulphonyl)amino]-9-(2-cyanoethyl)-1,2,3,4-tetrahydrocarbazole (enantiomer A)

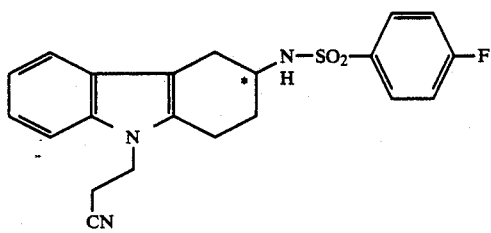

5.16 g (0.015 mol) of Example 65 are dissolved in 200 ml of dry dimethylformamide under nitrogen, and 0.5 g (0.0165 mol) of sodium hydride with 20% spindle oil is added in portions. Once evolution of hydrogen is complete, 2 ml (0.03 mol) of acrylonitrile are added to the reaction mixture. After stirring at room temperature for 1 h, 0.5 ml of acrylonitrile is once more added, and the mixture is stirred at room temperature for 1 h. It is diluted with 1 l of ethyl acetate and extracted three times with water.

The ethyl acetate phase is dried with sodium sulphate and evaporated. In this way 7.8 g of crude product is obtained and is chromatographed on 150 g of silica gel (0.063 to 0.2 mm, Merck) with a mixture of toluene/ethyl acetate in the ratio 1:1. A fraction which, after evaporation, provides 5.8 g (86% of theory) of product as a solid foam is obtained.

The bis-cyanoethyl adduct (3-[N-(4-fluorophenylsulphonyl)-N-(2-cyanoethyl)amino]-9-(2-cyanoethyl)-1,2,3,4-tetrahydrocarbazole) is produced under the conditions indicated in Example 6.

Example 68

3-[N-(4-Fluorophenylsulphonyl)-N-(2-cyanoethyl)amido]-9-(2-cyanoethyl)-1,2,3,4-tetrahydrocarbazole (enantiomer B)

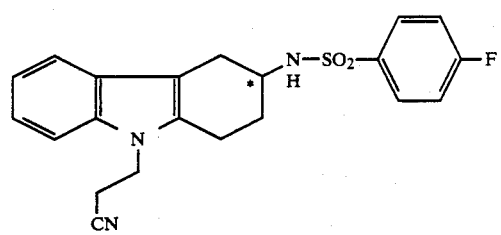

Example 68 is prepared from Example 66 in analogy to the preparation of Example 67 from Example 65.

Example 69

(+)-3-(4-Fluorophenylsulphonamido)-9-(2-carboxyethyl)-1,2,3,4-tetrahydrocarbazole

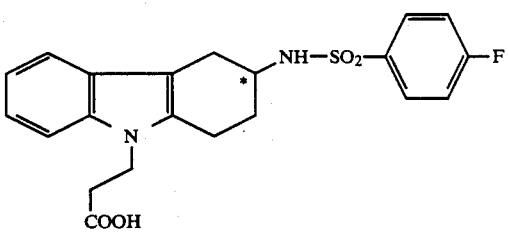

5.8 g (0.0128 mol) of Example 67 are dissolved in 60 ml of isopropanol, 130 ml of 10% strength potassium hydroxide solution are added and, after heating under reflux for 16 h, the mixture is cooled, diluted with water and extracted with ethyl acetate. The aqueous phase is concentrated in vacuo and then acidified dropwise with concentrated hydrochloric acid while stirring vigorously. The acid which precipitates out during this is filtered off with suction, washed with water and thoroughly dried in vacuo. 4.4 g (86.6% of theory) of the product are obtained.

Melting point: 85°-95° C.
Rotation $[\alpha]^{20} = 42.55°$ (CHCl$_3$)

Example 70

(−)-3-(4-Fluorophenylsulphonamido)-9-(2-carboxyethyl)-1,2,3,4-tetrahydrocarbazole

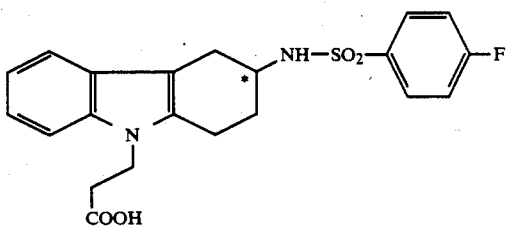

Example 70 is prepared from Example 68 in analogy to the preparation of Example 69 from Example 67.
Melting point: 85°-95° C. Rotation: $[\alpha]^{20} = -37.83°$ (CHCl$_3$)

Example 71

(+)-3-Amino-1,2,3,4-tetrahydrocarbazole

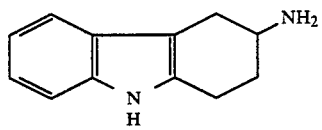

18.6 g (0.1 mol) of racemic 3-amino-1,2,3,4-tetrahydrocarbazole are heated together with 15.2 g (0.1 mol) of (+)-mandelic acid in 100 ml of tetrahydrofuran under reflux. Once a clear solution has been obtained, it is allowed to cool and a spatula tip of the (+)-mandelic acid salt of (+)-3-amino-1,2,3,4-tetrahydrocarbazole (enantiomer A, Example 59) is added as seed crystals. The mixture is stirred overnight, and the crystals which have separated out are filtered off with suction. In this way 6.05 g of enantiomerically enriched material are obtained. 4.7 g of these crystals are dissolved in 330 ml of boiling methyl isobutyl ketone and, after cooling slightly, the solution is seeded and stirred as cooling is continued. After filtration with suction and washing with methyl isobutyl ketone, 3.4 g of (+)-3-amino-1,2,3,4-tetrahydrocarbazole are obtained as the (+)-mandelic acid salt.

Example 72

For determination of the action inhibiting platelet aggregation use was made of blood from healthy subjects of both sexes. One part of 3.8% strength aqueous sodium citrate solution was mixed as anticoagulant with 9 parts of blood. Platelet-rich citrated plasma (PRP) is obtained from this blood by centrifugation (Jurgens/-Beller, Klinische Methoden der Blutgerinnungsanalyse (Chemical Methods of Blood Coagulation Analysis); published by Thieme, Stuttgart, 1959).

For these investigations, 0.8 ml of PRP and 0.1 ml of the active compound solution were preincubated in a waterbath at 37° C. Subsequently the platelet aggregation was determined by the turbidometric method in an aggregometer at 37° C. (Born, G. V. R., J. Physiol. (London), 162, 1962 and Therapeutische Berichte 47, 80–86, 1975). For this purpose, 0.1 ml of collagen, an aggregation-initiating agent, was added to the preincubated sample. The change in the optical density of the sample of PRP was recorded during a period of 6 minutes, and the deflection after 6 minutes was determined. For this purpose, the percentage inhibition compared with the control is calculated.

| Cycloalkano[1,2-b]indolesulphonamide of Example No. | Limiting concentration for inhibition (mg/kg) |
| --- | --- |
| 6 | 10–3 |
| 12 | 0.03–0.01 |
| 17 | 0.03–0.01 |
| 22 | 3–1 |
| 27 | 0.1–0.03 |
| 32 | 0.1–0.03 |
| 38 | 1.0–0.3 |
| 39 | 0.3–0.1 |
| 40 | 1.0–0.3 |
| 41 | 0.3–0.1 |
| 46 | 0.1–0.01 |
| 52 | 0.3–0.1 |

We claim:
1. A ketone of the formula

$$\text{structure with } (CH_2)_y-NH-SO_2-R^2 \text{ and } (CH_2)_x, \text{ O}$$

in which
R² represents phenyl which is substituted up to 5 times by halogen,
x represents the number 1, 2 or 3, and
y represents the number 1.
2. A ketone according to claim 1, in which
R² represents phenyl which is substituted up to three times, identically or differently, by fluorine, chlorine and bromine.

* * * * *

UNITED STATES PATENT AND TRADEMARK OFFICE
CERTIFICATE OF CORRECTION

PATENT NO. : 4,827,032
DATED : May 2, 1989
INVENTOR(S) : Horst Böshagen, et al

It is certified that error appears in the above-identified patent and that said Letters Patent is hereby corrected as shown below:

| | |
|---|---|
| Col. 1, line 20 | Middle of formula insert --¦-- as follows:  |
| Col. 3, line 59 | After "humans" insert --and animals.-- |
| Col. 4, line 26 | Delete "branches" and substitute --branched-- |
| Col. 13, line 64 | Delete "$R^{12}$" and substitute --$R^2$-- |
| Col. 14, line 20 | After "CA" delete "a" |
| Col. 14, line 67 | Correct spelling of --tetrahydrofuran-- |
| Col. 15, line 3 | Insert --in which-- |
| Col. 22, line 53 | Before "kieslgur" second instance insert --the-- |
| Col. 23, line 61 | Delete "0.082" and substitute --0.0826-- |
| Col. 24, line 32 | After "1.83 g" delete "20" |
| Col. 25, line 20 | Before "procedure" delete "the" second instance |
| Col. 25, line 59 | After "14.3" delete "Lg" and substitute --g-- |
| Col. 28, line 15 | After "chlorophenylsulphonyl" and before "-" insert --)-- |

UNITED STATES PATENT AND TRADEMARK OFFICE
CERTIFICATE OF CORRECTION

PATENT NO. : 4,827,032
DATED : May 2, 1989
INVENTOR(S) : Horst Böshagen, et al

It is certified that error appears in the above-identified patent and that said Letters Patent is hereby corrected as shown below:

Col. 32, lines 10, 46    Insert --  -- as follows:
                         -- 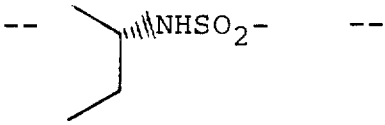 --

Col. 34, line 39         Delete "analog" and substitute --analogy--

Col. 44, line 41         After "bromine" insert --, x represents the number 1 or 2, and y represents the number 1.--

Signed and Sealed this

Sixteenth Day of January, 1990

Attest:

JEFFREY M. SAMUELS

*Attesting Officer*     Acting Commissioner of Patents and Trademarks